United States Patent
Watson

(10) Patent No.: US 9,176,031 B2
(45) Date of Patent: Nov. 3, 2015

(54) LABELING AND SAMPLE PREPARATION FOR SEQUENCING

(71) Applicant: Andrew Watson, Bedford, MA (US)

(72) Inventor: Andrew Watson, Bedford, MA (US)

(73) Assignee: Raindance Technologies, Inc., Billerica, MA (US)

( * ) Notice: Subject to any disclaimer, the term of this patent is extended or adjusted under 35 U.S.C. 154(b) by 0 days.

(21) Appl. No.: 13/774,437

(22) Filed: Feb. 22, 2013

(65) Prior Publication Data

US 2013/0225418 A1 Aug. 29, 2013

Related U.S. Application Data

(60) Provisional application No. 61/603,051, filed on Feb. 24, 2012.

(51) Int. Cl.
*C12Q 1/68* (2006.01)
*G01N 1/30* (2006.01)

(52) U.S. Cl.
CPC .............. *G01N 1/30* (2013.01); *C12Q 1/6806* (2013.01)

(58) Field of Classification Search
None
See application file for complete search history.

(56) References Cited

U.S. PATENT DOCUMENTS

2003/0148273 A1* 8/2003 Dong et al. ............... 435/6

OTHER PUBLICATIONS

Herzer (DNA Purification, in Molecular Biology Problem Solver: A Laboratory Guide, Edited by Alan S. Gerstein, Ch. 7, 2001).*
Roche (454 Sequencing System Guidelines for Amplicon Experimental Design, attached, May 2011).*
Illumina (Genomic Sequencing, data sheet, attached, 2010)).*
Hindson et al. (High-Throughput Droplet Digital PCR System for Absolute Quantitation of DNA Copy Number).*

* cited by examiner

*Primary Examiner* — Stephanie K Mummert
*Assistant Examiner* — Aaron Priest
(74) *Attorney, Agent, or Firm* — Brown Rudnick LLP; Thomas C. Meyers

(57) ABSTRACT

The invention provides methods for sequencing and sample preparation for sequencing and amplification.

21 Claims, 10 Drawing Sheets

Universal Binding Barcode Library: Components and Manufacturing

Universal Barcode Droplet Library: Sticky-ended Ligation Library Types

Universal Primer Extension Barcode Droplet Library Construction

Library contains primer pairs constructed such that 1) they will prime from the short fragments using complementary sequences A' and B', 2) they contain a code, CODE1, or set of codes, CODE1 and CODE2, that identify the droplet, and 3) there are (optionally) universal priming sites P1 and P2 for attaching the sequencing primers via PCR.

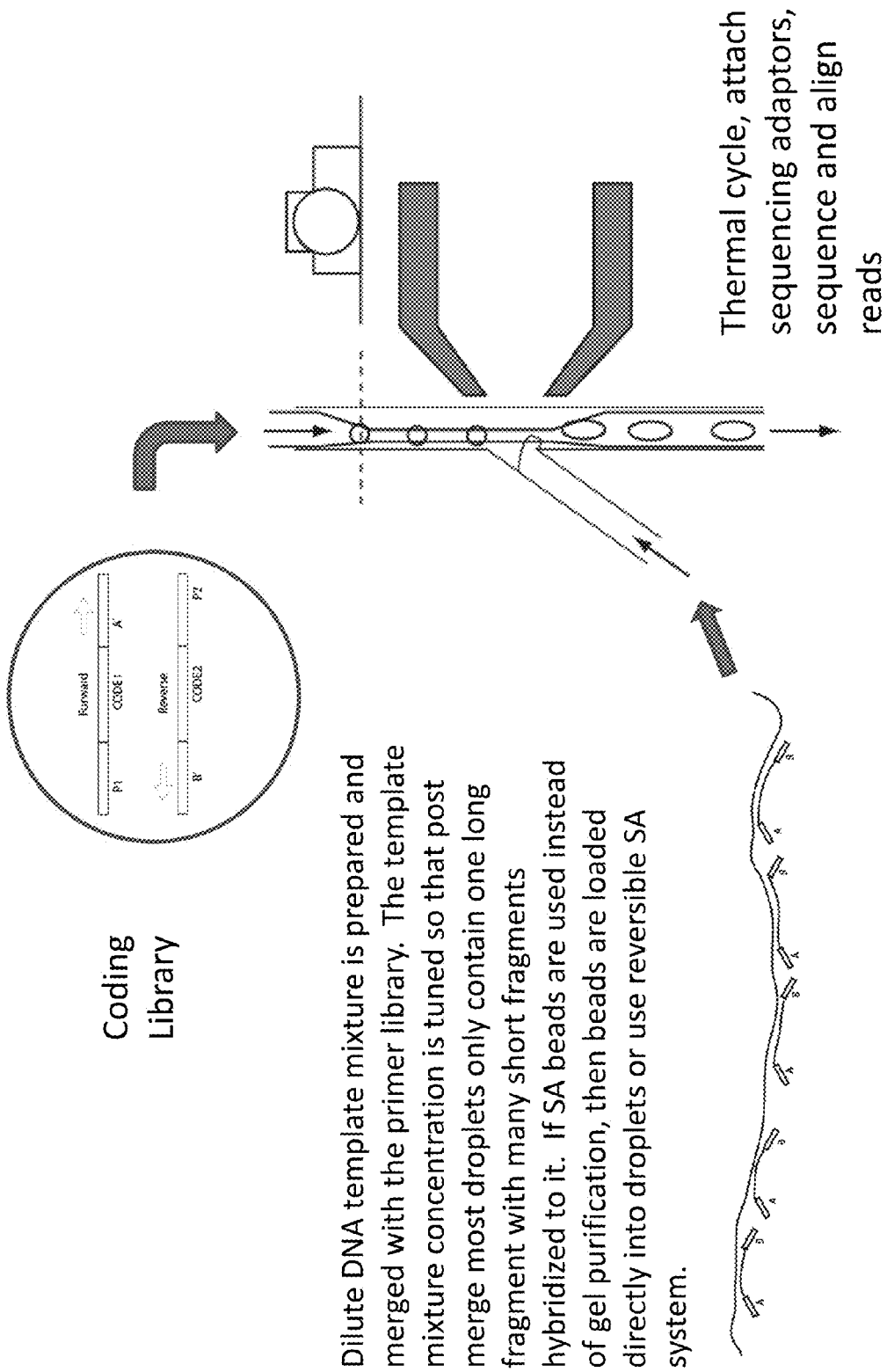

LABELING AND SAMPLE PREPARATION FOR SEQUENCING

RELATED APPLICATION

The present application claims the benefit of and priority to U.S. provisional application Ser. No. 61/603,051, filed Feb. 24, 2012, the content of which is incorporated by reference herein in its entirety.

FIELD OF THE INVENTION

The present invention generally relates to methods and materials for labeling and sequencing genomic DNA.

BACKGROUND OF THE INVENTION

The analysis of nucleic acids and proteins is an essential element of molecular biology. The ability to detect, discriminate, and utilize genetic and proteomic information allows sensitive and specific diagnostics, as well as the development of treatments. Most genetic and proteomic analysis requires labeling for detection of the analytes of interest. For example, in sequencing applications, nucleotides added to a template strand during sequencing-by-synthesis typically are labeled, or are intended to generate a label, upon incorporation into the growing strand. The presence of the label allows detection of the incorporated nucleotide.

SUMMARY OF THE INVENTION

The present invention provides materials and methods for the preparation of nucleic acids, including DNA and RNA (or cDNA) for sequencing. In general, methods utilize fragmentation of nucleic acid into short and long fragment populations in which the short fragments are tailed (e.g., by attaching an adaptor or adaptor sequence) on their 3' and 5' ends; and then tiled (hybridized) along the longer fragments to create hybridized fragments. Upon purification, the tiled fragments are exposed to a library of barcoded primers that target the ligated ends of the short fragments. The primers are then used to analyze hybridized fragments. Analysis can be by amplifying fragments (short) by, for example, end point PCR or QPCR; sequencing short fragments using coded primers as sequencing primers; or the short fragments can be melted from the hybridized fragments and detected by, for example, hybrid capture.

Numerous variations of the invention are apparent to the skilled artisan. For example, in a preferred embodiment, long fragments containing tiled short fragments hybridized thereto are gel purified and placed into aqueous droplets that are then merged with droplets comprising coded primers. Ideally, there is one long, tiled fragment per droplet. In that way, entire genome equivalents are sequenced in highly multiplexed and parallel reactions in which sequence reads are tracked via the coding in the primers used for sequencing. For purposes of the invention, a sample of, for example, genomic DNA is fragmented using known methods into short fragments and long fragments. The relative size of the short and long fragments must be such that two or more short fragments can tile (e.g., hybridize) to a single large fragment. In a preferred embodiment, short fragments are from about 100 bases to about 1000 bases and large fragments are from about 5 Kb to about 100 Kb.

Tiled long fragments (i.e., long fragments with two or more short fragments from the same sample hybridized thereto) are purified by means known in the art. For example, fragments can be gel purified. Alternatively, labeling elements, such as biotin, can be incorporated into long or short fragments for purification using, for example, streptavidin. Any available binding pairs can be used as an aid to purification of the tiled fragments (e.g., carbohydrate/lectin, antibody/antigen, and others known in the art).

Once tiled fragments are made, they are exposed to a library of forward and reverse primer pairs for use in sequencing. A preferred library is constructed such that the primers prime the short fragments using sequences that are complementary to the ligated ends and that contain a barcode that identifies the sample, or in the case of a merged droplet, the droplet itself. Ideally, the primer pairs contain different codes, but they can be the same. In addition, the primers may have optional universal priming sites for attaching the sequencing primers via PCR (as shown, for example, in FIG. 7).

The invention provides fluid compartments, such as droplets, for the sequestration, isolation, labeling, detection, identification, and analysis of nucleic acid. The invention further provides labels. Labels according to the invention include barcode-type labels and probe-type labels.

Principles of the invention can be applied to analyze all or a portion of genomic DNA, RNA (or cDNA). Techniques disclosed herein provide labeled materials isolated in fluid compartments for use with analytical techniques such as sequencing, haplotyping, and multiplex digital-PCR.

As disclosed herein, target material can be sequestered in a fluid compartment or partition such as a single droplet. Other reagents including labels (e.g., barcoded or optically-labeled N-mers) can be provided, optionally also sequestered in droplets. The other reagents can be introduced into the fluid partitions containing the target material, for example, by merging droplets, resulting in the labeling of the target molecules (e.g., by hybridization of N-mers to target nucleic acids). Target material can undergo optional processing such as selective enrichment, amplification, or capture on a substrate (e.g., beads). Where the labels are of the barcode type, the invention provides analytical methods including selective capture or enrichment, sequencing, haplotype phasing, genotyping, and improved sequence read assembly, as well as methods of producing barcode droplet libraries. Where the labels are of the probe-type, the invention provides novel digital PCR assays including multiplex assays.

Target material can be obtained from a sample, and can include nucleic acid, proteins, carbohydrates, or other materials. The sample may be a human tissue or body fluid. Exemplary body fluids include pus, sputum, semen, urine, blood, saliva, and cerebrospinal fluid.

In certain aspects, the invention provides fluidic compartments to contain all or a portion of a target material. In some embodiments, a compartment is droplet. While reference is made to "droplets" throughout the specification, that term is used interchangeably with fluid compartment and fluid partition unless otherwise indicated. A fluid compartment can be a slug, an area on an array surface, a globule, or a reaction chamber in a microfluidic device, such as for example, a microfluidic device fabricated using multilayer soft lithography (e.g., integrated fluidic circuits). Except where indicated otherwise, "droplet" is used for convenience and any fluid partition or compartment may be used.

A droplet according to the invention generally includes an amount of a first sample fluid in a second carrier fluid. Any technique known in the art for forming droplets may be used with methods of the invention. An exemplary method involves flowing a stream of the sample fluid containing the target material (e.g., nucleic acid template) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material.

The carrier fluid may be any fluid that is immiscible with the sample fluid. An exemplary carrier fluid is oil. In certain embodiments, the carrier fluid includes a surfactant, such as a fluorosurfactant.

The same method may be applied to create individual droplets that contain other reagents such as labels or reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases such as Taq polymerase, forward and reverse primers, deoxynucleotide triphosphates (dNTPs), and one or more buffers. Suitable reagents for conducting non-PCR amplification reactions include, for example, a high fidelity enzyme such as 029. Alternatively, a transposase can be used.

Either the droplets containing the first fluid, the droplets containing the second fluid, or both, may be formed and then stored in a library for later merging, aspects of certain implementations of which are described in U.S. Pub. 2010/0022414, hereby incorporated herein in its entirety for all purposes.

Once formed, droplets containing the target material can be merged with droplets containing other reagents. Merging can produce a set of droplets, each containing target and other reagents such as, in each droplet, a single nucleic acid template and heterogeneous mixture of primer pairs and probes. Merging can be accomplished, for example, in the presence of an electric field. Moreover, it is not required that both fluids be in the form of droplets when merging takes places. One exemplary method for merging of fluid portions with droplets is taught, for example, in co-pending U.S. Patent Application Nos. 61/441,985 and 13/371,222, the contents of each of which are incorporated by reference herein.

In certain embodiments, fluidic compartments are formed by providing one or more of a first fluid partition (e.g., a droplet) comprising a target material and a second fluid (e.g., as a fluid stream or within droplets) comprising a plurality of nucleic acid constructs, each containing a functional N-mer capable of hybridizing to a unique region of the target material, and a unique N-mer to label the target. The first and second fluids are merged to form a droplet. Merging can be accomplished by application of an electric field to the two fluids. In certain embodiments, the second fluid additionally contains reagents for conducting an amplification reaction, such as a polymerase chain reaction or a multiple displacement amplification reaction. Optionally, the genetic material can be fragmented or sheared using methods well known to those of skill in the art, for example, prior to sequestering into droplets or hybridizing to N-mers.

Methods of the invention can further include the step of amplifying or copying the tiled fragments in order to incorporate barcodes in a sequencable amplicon. In certain aspects of the invention, the amplified product is indicative of a haplotype. The nucleic acid template in each of the merged/formed droplets is amplified, e.g., by thermocycling the droplets under temperatures/conditions sufficient to conduct a PCR reaction. The resulting amplicons in the droplets can then be analyzed. For example, using probe-type labels, the presence or absence of the plurality of targets in the one or more droplets is detected optically, e.g., by the detectable label on the plurality of probes. Alternatively, amplicons can be sequenced and reads assembled based on the presence of barcode-type labels.

In some embodiments, capture sequences are introduced into droplets containing target material, for example, by merging the droplets with a second set of droplets containing the capture sequences. Capture sequences can include a barcode label and a portion that is capable of being captured on a solid surface (e.g., biotin/streptavidin on a surface; antibody/antigen; aptamers; anchored oligonucleotides; etc.). A droplet containing a nucleic acid can be merged with a second droplet containing the capture sequence, preferably with a tag (i.e., a barcode-type label). The capture sequence is allowed to hybridize to the target nucleic acid. The emulsion is then broken to release the hybridized capture sequence and target nucleic acid. The released nucleic acid is then captured on a solid support allowing the removal of elements such as cell debris, proteases and detergents that may inhibit subsequent steps. The tag is then incorporated by replication of the captured nucleic acid using the capture sequence with the tag as a primer. Replication can generate DNA from either DNA or RNA (cDNA synthesis). This material can either be processed directly or amplified further using methods known in the field such as PCR or multi-strand displacement amplification.

The capture sequences can be synthesized directly onto the beads or be attached by such means as biotinylated sequences and streptavidin beads. The use of streptavidin beads and biotinylated sequences has the advantage of allowing a generic bead to be used with new libraries of biotinylated capture sequences that can be assembled on demand. However, any method known in the art for attaching nucleic acid sequences to beads can be utilized.

In certain embodiments, droplets containing target material may be merged with droplets containing beads that are designed to capture the target. After capture, the emulsion (i.e., set of droplets) is broken and the beads are used to purify the target away from other components of the reaction that may inhibit subsequent steps such as cell debris, proteases and detergents. Target (e.g., nucleic acid) can be captured on beads by using random N-mers designed to capture all sequences. In some embodiments, N-mers that are designed to capture only portions of the target are attached to the beads. Where the N-mers include a barcode-type tag, the tag can be incorporated by replication of the captured nucleic acid using the capture sequence with the tag as a primer. The replication can generate DNA from DNA or RNA (cDNA synthesis). This material can either be processed directly or amplified further using methods known in the art such as PCR or multi-strand displacement amplification.

In certain embodiments, methods of the invention include enriching all or selected portions of a target material. N-mers can be provided that further contain a common nucleotide sequence, such as a universal PCR sequence. In an exemplary embodiment, the enrichment step is accomplished by incorporating an adapter onto the 5' end of the amplified genetic material, such as a universal PCR primer sequence, and further amplifying the genetic material. Only those strands having a label will be amplified, thereby enriching for the labeled genetic material. Alternatively, enrichment of sequence specific labeled strands can be achieved through amplification using a primer specific for the universal priming sequence incorporated into the labeled strand, and a primer specific for a desired target sequence. An enrichment step can be specific for target regions of interest in the genetic material, such as consensus sequences like CPG motifs, or other sequence motifs that are related to known or suspected sequences indicative of splice sites, promoter regions, regulatory regions, poly-A tail etc. In some embodiments, a first portion of amplified product associated with the label is enriched relative to a second portion of amplified product not associated with the label (e.g., through the inclusion of universal priming sites with the label).

Suitable sequencing methods for use in the invention include, but are not limited to, sequencing by hybridization, sequencing by synthesis technology (e.g., HiSeq™ and Solexa™, Illumina), SMRT™ (Single Molecule Real Time) technology (Pacific Biosciences), true single molecule sequencing (e.g., HeliScope™, Helicos Biosciences), massively parallel next generation sequencing (e.g., SOLiD™, Applied Biosciences; Solexa and HiSeq™, Illumina), massively parallel semiconductor sequencing (e.g., Ion Torrent), and pyrosequencing technology (e.g., GS FLX and GS Junior Systems, Roche/454).

A barcode library for use in the invention can comprise a plurality of fluid compartments, each containing one or more copies of a unique construct, in which each construct includes a unique N-mer and a functional N-mer. For a universal barcode library of general applicability, each functional N-mer may be a sticky end, capable of being associated with another sticky end. Other functional N-mers can include sequence-specific primers; random N-mers; antibodies; probe targets; and universal primer sites. The fluid compartments can be water-in-oil droplets. The unique N-mer offers a barcode of information and can generally be between about 2 and 21 nucleotides in length, and optional longer, e.g., up to 50, 100, or any length.

In certain aspects, the invention relates to methods for detecting or identifying (e.g., by sequencing) one or a plurality of targets in a biological sample using digital PCR in fluid partitions. Methods of the invention include labeling target material with a probe-type label. A probe type label can include an optical label, and labeled target material can be identified or analyzed using digital PCR.

In some embodiments, the invention provides microfluidic droplets for multiplex analysis. Each droplet can contain a plurality of probes that hybridize to amplicons produced in the droplets. Preferably, the droplet contains two or more probes, e.g., 2, 3, 4, 5, 6, 7, 8, 9, 10, 12, 14, 16, 18, 20, 25, 30, 35, 40, 45, 50, 55, 60, 65, 60, 75, 80, 85, 90, 95, 100, 110, 120, 130, 140, 150, 160, 170, 180, 190, 200, 500, or more probes.

The ability to amplify and detect single nucleic acids in droplets enables digital PCR, detection, counting, and differentiation among nucleic acids, especially those present in heterogeneous samples. Thus, the invention applies to digital amplification techniques and, in specific embodiments enables multiplex PCR in droplets. For example, multiplexing primers in droplets enables the simultaneous increase in the number of PCR droplets while keeping the amount of input DNA the same or lower and generate the same or greater amplicon yield. This results in an overall increase in the amount of PCR positive droplets and amplicon yield without the consumption of more DNA. In some embodiments, even though the number of PCR primer pairs per droplet is greater than one, there is only one template molecule per droplet, and thus, in some implementations, there is only one primer pair per droplet that is being utilized at one time. As such, the advantages of droplet PCR for eliminating bias from either allele specific PCR or competition between different amplicons is maintained. However, as described below in relation to detection of haplotypes, other implementations advantageously allow detection of multiple loci on a single template using multiple primer pairs, preferably designed to minimize bias.

In certain aspects, the invention provides methods of forming fluid partitions including target and reagents for digital PCR in which the methods enable multiplex digital PCR at high "plexity" in fluid partitions. In some embodiments, one or more droplets are formed, each containing a single nucleic acid template and a heterogeneous mixture of primer pairs and probes, each specific for multiple target sites on the template. For example, a first fluid (either continuous, or discontinuous as in droplets) containing a single nucleic acid template (DNA or RNA) is merged with a second fluid (also either continuous, or discontinuous as in droplets) containing a plurality of primer pairs and a plurality of probes, each specific for multiple target sites on the nucleic acid template, to form a droplet containing the single nucleic acid template and a heterogeneous mixture of primer pairs and probes. The second fluid can also contain reagents for conducting a PCR reaction, such as a polymerase and dNTPs. The droplet contents can be amplified (e.g., by thermocycling). The probes are hybridized to the amplicons and hybridization is optically detected.

BRIEF DESCRIPTION OF THE DRAWINGS

In the drawings, like reference characters generally refer to the same or similar parts throughout the different views. Also, the drawings are not necessarily to scale, emphasis instead generally being placed upon illustrating the principles of the invention.

In the drawings, like reference characters generally refer to the same or similar parts throughout the different views. Also, the drawings are not necessarily to scale, emphasis instead generally being placed upon illustrating the principles of the invention.

FIG. 10 shows an exemplary method of introducing the longer fragments having smaller fragments bound thereto to droplets including the primer pairs. In this embodiments, the droplets are flowing through a channel until they reach a merge point where a bolus of aqueous fluid including the longer fragments is growing into the channel. The droplet comes in contact with the bolus in the presence of an electric field, which causes the bolus to break-off from the fluid flow and form a mixed droplet.

DETAILED DESCRIPTION

Figure 1A:
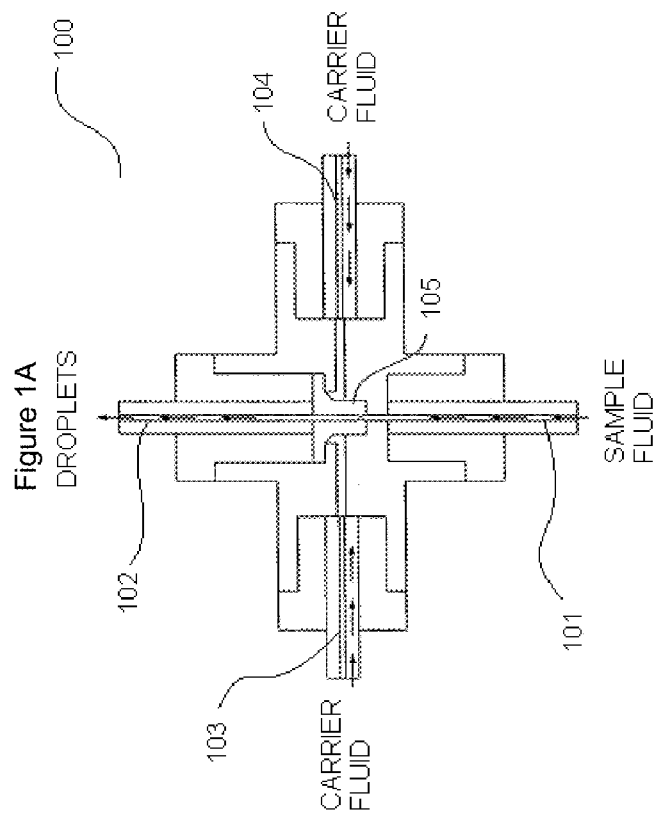
FIG. 1A depicts a droplet formation device.

The invention provides sample preparation methods and constructs for identifying and sequencing nucleic acids. In a preferred embodiment, genomic DNA is fragmented into short and long fragments. The short fragments are tailed on their 3' and 5' ends, which can be done by ligation, amplification or by other methods known in the art. The short fragments are hybridized along the length of the large fragments (i.e., tiled); and the resulting construct is purified and exposed to primers for sequencing and/or amplification. In a preferred embodiment, tiled fragments are placed into an aqueous droplet in an immiscible fluid and merged with primers for sequencing and/or amplification. In a preferred embodiment, the primers are in a droplet and the droplets are merged as described below.

Microfluidic Systems

Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some cases. In some cases, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

Specifically, the devices and methods described herein are based on the creation and manipulation of aqueous phase droplets (e.g., droplet libraries) surrounded by an immiscible carrier fluid. This combination enables precise droplet generation, highly efficient, electrically addressable droplet coalescence, and controllable, electrically addressable single droplet sorting.

Generally, microfluidic devices include one or more channels in one or more analysis units. An "analysis unit" is a microsubstrate, e.g., a microchip. The terms microsubstrate, substrate, microchip, and chip are used interchangeably herein. An analysis unit typically includes at least an inlet channel and a main channel. The analysis unit can further include coalescence, detection, or sorting modules. The sorting module can be in fluid communication with branch channels which are in fluid communication with one or more outlet modules (e.g., collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A plurality of analysis units of the invention may be combined in one device. The dimensions of the substrate are those of typical microchips, ranging between about 0.5 cm to about 15 cm per side and about 1 micron to about 1 cm in thickness. The analysis unit and specific modules are described in further detail in WO 2006/040551; WO 2006/040554; WO 2004/002627; WO 2004/091763; WO 2005/021151; WO 2006/096571; WO 2007/089541; WO 2007/081385 and WO 2008/063227.

A variety of materials and methods can be used to form devices of the invention. For example, components can be formed from solid materials, in which the channels can be formed via molding, micromachining, film deposition processes such as spin coating and chemical vapor deposition, laser fabrication, photolithographic techniques, etching methods including wet chemical or plasma processes, and the like. See, for example, Angell, et al., Scientific American, 248:44-55, 1983. At least a portion of the fluidic system can be formed of silicone by molding a silicon chip. Devices of the invention can also be formed of a polymer, for example, an elastomeric polymer such as poly-dimethylsiloxane (PDMS), polytetrafluoroethylene (PTFE), Teflon®, or the like. PDMS polymers include those sold under the trademark Sylgard by Dow Chemical Co., Midland, Mich., and particularly Sylgard 182, Sylgard 184, and Sylgard 186. Silicone polymers such as PDMS are generally inexpensive, readily available, and can be solidified from a prepolymeric liquid via curing with heat. For example, PDMS is typically curable by exposure of the prepolymeric liquid to temperatures of about, for example, about 65° C. to about 75° C. for exposure times of, for example, about an hour. Also, silicone polymers can be elastomeric and thus may be useful for forming very small features with relatively high aspect ratios, necessary in certain embodiments of the invention.

Because PDMS can be oxidized, for example by exposure to an oxygen-containing plasma such as an air plasma, devices of the invention may contain, at their surface, chemical groups capable of cross-linking to other oxidized silicone polymer surfaces or to the oxidized surfaces of a variety of other polymeric and non-polymeric materials. Thus, components can be formed and then oxidized and essentially irreversibly sealed to other silicone polymer surfaces or to the surfaces without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Further, PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Molding, oxidation and sealing methods are described in the art, for example, in Duffy et al., "Rapid Prototyping of Microfluidic Systems and Polydimethylsiloxane," Anal. Chem., 70:474-480, 1998.

Another advantage of oxidized silicone polymers is that these surfaces can be much more hydrophilic than the surfaces of typical elastomeric polymers (where a hydrophilic interior surface is desired).

Thus, a channel can have a hydrophilic surface, which can be more easily wetted compared to other surfaces, which makes the channel easier to fill with aqueous solutions Generally, "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet. A channel can be formed, for example by etching a silicon chip using conventional photolithography techniques, or using a micromachining technology called "soft lithography" as described by Whitesides and Xia, Angewandte Chemie International Edition 37, 550 (1998).

A fluid within a channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases.

Channels can be configured to coalesce droplets or to flow material by a detection module or a sorting module. A main channel is typically in fluid communication with any coalescence, detection and/or sorting modules, as well as inlet, branch, or outlet channels and any collection or waste modules. These channels permit the flow of molecules, cells, small molecules or particles out of the main channel. An "inlet channel" permits the flow of molecules, cells, small molecules or particles into the main channel. One or more inlet channels communicate with one or more means for introducing a sample into the device of the present invention. A microfluidic device can also include fluid channels to inject or remove fluid in between droplets in a droplet stream for the purpose of changing the spacing between droplets.

A microfluidic substrate can also include a specific geometry designed to prevent the aggregation of material prior to encapsulation in droplets. The geometry of channel dimension can be changed to disturb the aggregates and break them apart by various methods, that can include, but is not limited to, geometric pinching (to force cells or particles through a narrow region, whose dimension is smaller or comparable to the dimension of a single cell) or a barricade (place a series of barricades on the way of the moving cells to disturb the movement and break up the aggregates of cells).

To prevent target material (e.g., cells, molecules, or other material as discussed below) from adhering to the sides of the channels, the channels (and coverslip, if used) may have a coating to minimize adhesion. The surface of the channels can be coated with any anti-wetting or blocking agent for the dispersed phase. The channel can be coated with any protein to prevent adhesion of the biological/chemical sample. Channels can be coated by any means known in the art. For example, the channels can be coated with Teflon®, BSA, PEG-silane and/or fluorosilane in an amount sufficient to prevent attachment and prevent clogging. In another example, the channels can be coated with a cyclized transparent optical polymer obtained by copolymerization of perfluoro (alkenyl vinyl ethers), such as the type sold by Asahi Glass Co. under the trademark Cytop. In such an example, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of perfluoro-alkylalkylsilane, described in U.S. Pat. No. 5,523,162. The surface of the channels in the microfluidic device can be also fluorinated by any means known in the art to prevent undesired wetting behaviors. For example, a microfluidic device can be placed in a polycarbonate dessicator with an open bottle of (tridecafluoro-1,1,2,2-tetrahydrooctyl) trichlorosilane. The dessicator is evacuated for 5 minutes, and then sealed for 20-40 minutes. The dessicator is then back-filled with air and removed. This approach uses a simple diffusion mechanism to enable facile infiltration of channels of the microfluidic device with the fluorosilane and can be readily scaled up for simultaneous device fluorination. By fluorinating the surfaces of the channels, the continuous phase preferentially wets the channels and allows for the stable generation and movement of droplets through the device. The low surface tension of the channel walls thereby minimizes the accumulation of channel clogging particulates, enhancing the processing of target material.

Target Material

Target material is any nucleic acid, including DNA, RNA, cDNA, PNA, LNA and others. Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule and serve as a surrogate for quantifying and/or detecting the target molecule. Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures).

Proteins or portions of proteins (amino acid polymers) that can bind to high affinity binding moieties, such as antibodies or aptamers, are target molecules for oligonucleotide labeling, for example, in droplets, in some embodiments of this invention.

Droplet Formation

Methods of the invention involve forming droplets, which may contain no target material, target material from a single cell (e.g., a nucleic acid such as genomic DNA or expressed RNA), all or a portion of a target from a single cell, or all or a portion of target from multiple cells (corresponding to limiting or terminal dilution, respectively, as defined above).

In certain embodiments, the distribution of material within droplets obeys the Poisson distribution. However, methods for non-Poisson loading of droplets are known to those familiar with the art, and include but are not limited to active sorting of droplets, such as by laser-induced fluorescence, or by passive one-to-one loading.

The droplets are aqueous droplets that are surrounded by an immiscible carrier fluid. Methods of forming such droplets are discussed in U.S. Pub. 2008/0014589; U.S. Pub. 2008/0003142; U.S. Pub. 2010/0137163; U.S. Pat. No. 7,708,949; U.S. Pub. 2010/0172803; and U.S. Pat. No. 7,041,481, the content of each of which is incorporated by reference herein in its entirety.

Figure 1B:
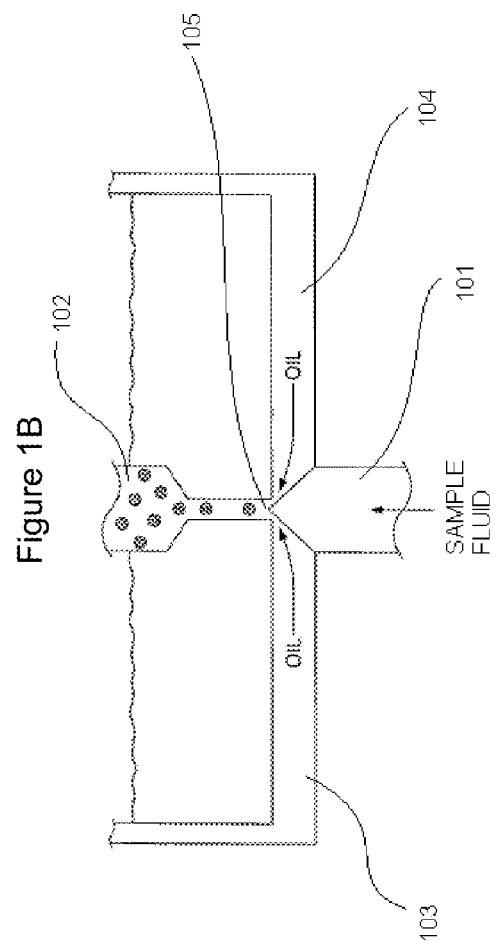
FIG. 1B depicts a portion of the droplet formation device of FIG. 1A.

FIG. 1A shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 1B). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with target material can be used. The carrier fluid is immiscible with the sample fluid. The carrier fluid can be a non-polar solvent, decane (e.g., tetradecane or hexadecane), fluorocarbon oil, silicone oil or another oil (e.g., mineral oil).

In certain embodiments, the carrier fluid contains one or more additives, such as agents which increase, reduce, or otherwise create non-Newtonian surface tensions (surfactants) and/or stabilize droplets against spontaneous coalescence on contact. Surfactants can include Tween, Span, fluorosurfactants, and other agents that are soluble in oil relative to water. Suitable surfactants are known in the art. In some applications, performance is improved by adding a second surfactant, or other agent, such as a polymer or other additive, to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant or a mixture of surfactants. In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with ammonium hydroxide in a fluorinated solvent. The solvent, water, and ammonia can be removed with a rotary evaporator. The surfactant can then be dissolved (e.g., 2.5 wt %) in a fluorinated oil (e.g., Flourinert (3M)), which then serves as the carrier fluid.

Another approach to merging sample fluids involves forming a droplet, and contacting the droplet with a fluid stream, in which a portion of the fluid stream integrates with the droplet to form a mixed droplet.

A droplet is formed as described above. After formation of the sample droplet from the first sample fluid, the droplet is contacted with a flow of a second sample fluid stream. Contact between the droplet and the fluid stream results in a portion of the fluid stream integrating with the droplet to form a mixed droplet, which, as discussed below, form a basis for droplet libraries according to certain embodiments of the invention.

The monodisperse droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first or second sample fluids. Applying electric charge is described in U.S. Pub. 2007/0003442, the content of which is incorporated by reference herein in its entirety. Electric charge may be created in a sample fluid within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of a bolus of the second sample fluid and the first sample fluid droplet. The forming mixed droplet continues to increase in size until breaks free from the second sample fluid stream, for instance prior to the arrival of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel (e.g., for possible use in a droplet library).

Where material in droplets will be subject to PCR, those droplets can be merged with a second fluid containing reagents for a PCR reaction (e.g., Taq polymerase, dNTPs, magnesium chloride, and forward and reverse primers, all suspended within an aqueous buffer). The second fluid may also include detectably labeled probes and/or universal barcodes for detection of the amplified target material, the details of which are discussed below. A droplet containing the target or portion thereof is then caused to merge with the PCR reagents in the second fluid as described above, producing a droplet that includes target and PCR reagents as well as, optionally, detectably labeled probes.

Droplet Libraries

Droplet libraries are useful to perform large numbers of assays while consuming only limited amounts of reagents. A "droplet," as used herein, is an isolated portion of a first fluid that is surrounded by a second fluid. In some cases, the droplets may be spherical or substantially spherical; however, in other cases, the droplets may be non-spherical, for example, the droplets may have the appearance of "blobs" or other irregular shapes, for instance, depending on the external environment. In some embodiments, a droplet is a first fluid completely surrounded by a second fluid. As used herein, a first entity is "surrounded" by a second entity if a closed loop can be drawn or idealized around the first entity through only the second entity (with the sometimes exception for portions of the first fluid that may be in contact with a wall or other boundary, where applicable).

In general, a droplet library is made up of a number of library elements that are pooled together in a single collection. Libraries may vary in complexity from a single library element to 1015 library elements or more. Each library element is one or more given components at a fixed concentration. The element may be, but is not limited to, cells, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element can include, but is not limited to, hybridomas, B-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8):1262-1264, 2008. The discreet nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element contains one or more beads, and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, the library elements will be prepared from a variety of starting fluids.

Often it is desirable to have exactly one cell per droplet with only a few droplets containing more than one cell when starting with a plurality of cells. In some cases, variations from Poisson statistics can be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. The droplets range in size from roughly 0.5 micron to 500 micron in diameter, which corresponds to about 1 pico liter to 1 nano liter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are preferably uniform in size. That is, the diameter of any droplet within the library will vary less than 5%, 4%, 3%, 2%, 1% or 0.5% when compared to the diameter of other droplets within the same library. The uniform size of the droplets in the library is critical to maintain the stability and integrity of the droplets and is also essential for the subsequent use of the droplets within the library for the various biological and chemical assays described herein.

In certain embodiments, the droplet libraries are using an immiscible fluorocarbon oil. The oil can comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that can be utilized in the droplet libraries of the present invention are described in greater detail herein.

The droplet libraries of the present invention are very stable and are capable of long-term storage. The droplet libraries are determined to be stable if the droplets comprised within the libraries maintain their structural integrity, that is the droplets do not rupture and elements do not diffuse from the droplets. The droplets libraries are also determined to be stable if the droplets comprised within the libraries do not coalesce spontaneously (without additional energy input, such as electrical fields described in detail herein). Stability can be measured at any temperature. For example, the droplets are very stable and are capable of long-term storage at any temperature; for example, e.g., $-70°$ C., $0°$ C., $4°$ C., $37°$ C., room temperature, $75°$ C. and $95°$ C. Specifically, the droplet libraries of the present invention are stable for at least 30 days. More preferably, the droplets are stable for at least 60 days. Most preferably, the droplets are stable for at least 90 days.

The invention provides a droplet library comprising a plurality of aqueous droplets within an immiscible fluid (optionally comprising a fluorosurfactant), wherein each droplet is preferably substantially uniform in size and comprises a different library element. The invention provides a method for forming the droplet library comprising providing a single aqueous fluid comprising different library elements, encapsulating each library element into an aqueous droplet within an immiscible fluid (optionally comprising a fluorosurfactant).

In certain embodiments, different types of elements (e.g., cells or beads), are pooled in a single source contained in the same medium. After the initial pooling, the elements are then encapsulated in droplets to generate a library of droplets wherein each droplet with a different type of bead or cell is a different library element. The dilution of the initial solution enables the encapsulation process. In some embodiments, the droplets formed will either contain a single element or will not contain anything, i.e., be empty. In other embodiments, the droplets formed will contain multiple copies of a library element. The elements being encapsulated are generally variants of a type. In one example, elements are cancer cells of a tissue biopsy, and each cell type is encapsulated to be screened for genomic data or against different drug therapies. Another example is that 1011 or 1015 different type of bacteria; each having a different plasmid spliced therein, are encapsulated. One example is a bacterial library where each library element grows into a clonal population that secretes a variant on an enzyme.

In certain embodiments, a droplet library comprises a plurality of aqueous droplets within an immiscible fluid, such that there is a single molecule contained within a droplet for every 20-60 droplets produced (e.g., 20, 25, 30, 35, 40, 45, 50, 55, 60 droplets, or any integer in between). Single molecules are encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 µm droplets were made at 10 kHz per second. Formation of these libraries relies on limiting dilutions.

The present invention also provides a droplet library comprising at least a first aqueous droplet and at least a second aqueous droplet within a fluorocarbon oil comprising at least one fluorosurfactant, wherein the at least first and the at least second droplets are uniform in size and comprise a different aqueous fluid and a different library element. The present invention also provides a method for forming the emulsion library comprising providing at least a first aqueous fluid comprising at least a first library of elements, providing at least a second aqueous fluid comprising at least a second library of elements, encapsulating each element of said at least first library into at least a first aqueous droplet within an immiscible fluorocarbon oil comprising at least one fluorosurfactant, encapsulating each element of said at least second library into at least a second aqueous droplet within an immiscible fluorocarbon oil comprising at least one fluorosurfactant, wherein the at least first and the at least second droplets are uniform in size and comprise a different aqueous fluid and a different library element, and pooling the at least first aqueous droplet and the at least second aqueous droplet within an immiscible fluorocarbon oil comprising at least one fluorosurfactant thereby forming an emulsion library.

For example, in one type of emulsion library, there are library elements that have different particles, i.e., cells or beads in a different medium and are encapsulated prior to pooling. In one example, a specified number of library elements, i.e., n number of different cells or beads, are contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevent the exchange of the contents of the library between droplets.

Droplet Sorting

Methods of the invention may further include sorting the droplets based upon whether the droplets contain a homogeneous population of molecules or a heterogeneous population of molecules. A sorting module may be a junction of a channel where the flow of droplets can change direction to enter one or more other channels, e.g., a branch channel, depending on a signal received in connection with a droplet interrogation in the detection module. Typically, a sorting module is monitored and/or under the control of the detection module, and therefore a sorting module may correspond to the detection module. The sorting region is in communication with and is influenced by one or more sorting apparatuses.

A sorting apparatus includes techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A branch channel is a channel that is in communication with a sorting region and a main channel. The main channel can communicate with two or more branch channels at the sorting module or branch point, forming, for example, a T-shape or a Y-shape. Other shapes and channel geometries may be used as desired. Typically, a branch channel receives droplets of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In certain embodiments, a fluidic droplet is sorted or steered by inducing a dipole in the uncharged fluidic droplet (which may be initially charged or uncharged), and sorting or steering the droplet using an applied electric field. The electric field may be an AC field, a DC field, etc. For example, a channel containing fluidic droplets and carrier fluid, divides into first and second channels at a branch point. Generally, the fluidic droplet is uncharged. After the branch point, a first electrode is positioned near the first channel, and a second electrode is positioned near the second channel. A third electrode is positioned near the branch point of the first and second channels. A dipole is then induced in the fluidic droplet using a combination of the electrodes. The combination of electrodes used determines which channel will receive the flowing droplet. Thus, by applying the proper electric field, the droplets can be directed to either the first or second channel as desired. Further description of droplet sorting is shown in U.S. Pub. 2008/0014589; U.S. Pub. 2008/0003142, and U.S. Pub. 2010/0137163.

Based upon the detected signal at the detection module, droplets containing a heterogeneous population of molecules are sorted away from droplets that contain a homogeneous population of molecules. Droplets may be further sorted to separate droplets that contain a homogeneous population of amplicons of the target from droplets that contain a homogeneous population of amplicons of the variant of the target.

Target Amplification

Methods of the invention may further involve amplifying the target genetic material in each droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other and by cycling parameters, and therefore, this length is a controllable parameter.

The sample droplet may be pre-mixed with a primer or primers, or the primer or primers may be added to the droplet. In some embodiments, droplets created by segmenting the starting sample are merged with a second set of droplets including one or more primers for the target nucleic acid in order to produce final droplets.

In embodiments involving merging of droplets, two droplet formation modules are used. In one embodiment, a first droplet formation module produces the sample droplets consistent with limiting or terminal dilution of target nucleic acid. A second droplet formation or reinjection module inserts droplets that contain reagents for a PCR reaction. Such droplets generally include the "PCR master mix" (known to those in the art as a mixture containing at least Taq polymerase, deoxynucleotides of type A, C, G and T, and magnesium chloride) and forward and reverse primers (known to those in the art collectively as "primers"), all suspended within an aqueous buffer. The second droplet also includes detectably labeled probes for detection of the amplified target nucleic acid, the details of which are discussed below. Different arrangements of reagents between the two droplet types is envisioned. For example, in another embodiment, the template droplets also contain the PCR master mix, but the primers and probes remain in the second droplets. Any arrangement of reagents and template DNA can be used according to the invention.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Another method for determining the melting temperature of primers is the nearest neighbor method (SantaLucia, "A unified view of polymer, dumbbell, and oligonucleotide DNA nearest-neighbor thermodynamics", 1998, P.N.A.S., 95 (4): 1460-5). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Com.

In one embodiment, the droplet formation modules are arranged and controlled to produce an interdigitation of sample droplets and PCR reagent droplets flowing through a channel. Such an arrangement is described U.S. Pub. 2008/0014589; U.S. Pub. 2008/0003142, and U.S. Pub. 2010/0137163.

A sample droplet is then caused to merge with a PCR reagent droplet, producing a droplet that includes the PCR master mix, primers, detectably labeled probes, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Further discussion can be found in U.S. Pub. 2007/0003442.

In another embodiment, called simple droplet generation, a single droplet formation module, or a plurality of droplet formation modules are arranged to produce droplets from a mixture already containing the template DNA, the PCR master mix, primers, and detectably labeled probes. In yet another embodiment, called co-flow, upstream from a single droplet formation module two channels intersect allowing two flow streams to converge. One flow stream contains one set of reagents and the template DNA, and the other contains the remaining reagents. In the preferred embodiment for co-flow, the template DNA and the PCR master mix are in one flow stream, and the primers and probes are in the other. On convergence of the flow streams in a fluidic intersection, the flow streams may or may not mix before the droplet generation nozzle. In either embodiment, some amount of fluid from the first stream, and some amount of fluid from the second stream are encapsulated within a single droplet. Following encapsulation, complete mixing occurs.

Once final droplets have been produced by any of the droplet forming embodiments above, or by any other embodiments, the droplets are thermal cycled, resulting in amplification of the target nucleic acid in each droplet. In certain embodiments, the droplets are collected off-chip as an emulsion in a PCR thermal cycling tube and then thermally cycled in a conventional thermal cycler. Temperature profiles for thermal cycling can be adjusted and optimized as with any conventional DNA amplification by PCR.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001).

In certain embodiments, the three temperature zones are controlled to have temperatures as follows: 95° C. ($T_H$), 55° C. ($T_L$), 72° C. ($T_M$). The prepared sample droplets flow through the channel at a controlled rate. The sample droplets first pass the initial denaturation zone ($T_H$) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. Methods for controlling the temperature in each zone may include but are not limited to electrical resistance, peltier junction, microwave radiation, and illumination with infrared radiation.

The nucleic acids undergo the same thermal cycling and chemical reaction as the droplets passes through each thermal cycle as they flow through the channel. The total number of cycles in the device is easily altered by an extension of thermal zones or by the creation of a continuous loop structure. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. ($T_H$) and 60° C. ($T_L$). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

In another embodiment the droplets are created and/or merged on chip followed by their storage either on the same chip or another chip or off chip in some type of storage vessel such as a PCR tube. The chip or storage vessel containing the droplets is then cycled in its entirety to achieve the desired PCR heating and cooling cycles.

In another embodiment the droplets are collected in a chamber where the density difference between the droplets and the surrounding oil allows for the oil to be rapidly exchanged without removing the droplets. The temperature of the droplets can then be rapidly changed by exchange of the oil in the vessel for oil of a different temperature. This technique is broadly useful with two and three step temperature cycling or any other sequence of temperatures.

Release from Droplet

Methods of the invention may further involve releasing amplified target molecules from the droplets for further analysis. Methods of releasing amplified target molecules from the droplets are shown in publications and patents referenced above.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

The released amplified material can also be subjected to further amplification by the use tailed primers and secondary PCR primers. In this embodiment the primers in the droplet contain an additional sequence or tail added onto the 5' end of the sequence specific portion of the primer. The sequences for the tailed regions are the same for each primer pair and are incorporated onto the 5' portion of the amplicons during PCR cycling. Once the amplicons are removed from the droplets, another set of PCR primers that can hybridize to the tail regions of the amplicons can be used to amplify the products through additional rounds of PCR. The secondary primers can exactly match the tailed region in length and sequence or can themselves contain additional sequence at the 5' ends of the tail portion of the primer.

During the secondary PCR cycling these additional regions also become incorporated into the amplicons. These additional sequences can include, but are not limited to: adaptor regions utilized by sequencing platforms for library preparation; barcode sequences for the identification of samples multiplexed into the same reaction; molecules for the separation of amplicons from the rest of the reaction materials (e.g., biotin, digoxin, peptides, or antibodies); or molecules such as fluorescent markers that can be used to identify the fragments.

In certain embodiments, the amplified target molecules are sequenced. In a particular embodiment, the sequencing is single-molecule sequencing-by-synthesis. Single-molecule sequencing is shown in U.S. Pat. Nos. 7,169,560; 6,818,395; 7,282,337; U.S. Pub. 2002/0164629; and Braslaysky, et al., PNAS (USA), 100: 3960-3964 (2003), the contents of each of these references are incorporated by reference herein in its entirety.

Briefly, a single-stranded nucleic acid (e.g., DNA or cDNA) is hybridized to oligonucleotides attached to a surface of a flow cell. The single-stranded nucleic acids may be captured by methods known in the art, such as those shown in U.S. Pat. No. 7,666,593. The oligonucleotides may be covalently attached to the surface or various attachments other than covalent linking as known to those of ordinary skill in the art may be employed. Moreover, the attachment may be indirect, e.g., via the polymerases of the invention directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

II. Barcode-Type Labels

Barcode Sequences

The invention involves the creation of specific barcodes for incorporation into primers for sequencing and/or amplification. Barcodes are used to identify the sample from which a nucleic acid was derived and/or the droplet containing it.

Attaching barcode sequences to nucleic acids is shown in U.S. Pub. 2008/0081330 and PCT/US09/64001, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6235,475; 7,393,665; 7,544,473; 5,846,719; 5,695,934; 5,604,097; 6,150,516; RE39,793; U.S. Pat. Nos. 7,537,897; 6,172,218; and 5,863,722, the content of each of which is incorporated by reference herein in its entirety.

Barcode sequences typically include a set of oligonucleotides ranging from about 4 to about 20 oligonucleotide bases (e.g., 8-10 oligonucleotide bases), which uniquely encode a discrete library member preferably without containing significant homology to any sequence in the targeted genome. The barcode sequence generally includes features useful in sequencing reactions. For example the barcode sequences are designed to have minimal or no homopolymer regions, i.e., 2 or more of the same base in a row such as AA or CCC, within the barcode sequence. The barcode sequences are also designed so that they are at least one edit distance away from the base addition order when performing base-by-base sequencing, ensuring that the first and last base do not match the expected bases of the sequence.

Synthesis of oligonucleotides for use as constructs (e.g., barcodes or functional portions) can be by any means known in the art. Oligonucleotides can be synthesized on arrays, or in bulk, for example.

In certain embodiments, the barcode sequences are designed to be correlated to a particular patient, allowing patient samples to be distinguished. The barcode sequences incorporated into a plurality of primers (and subsequently into DNA or RNA targets) within a single droplet may be the same, and vary from droplet to droplet. Alternatively, the barcode sequences incorporated into the plurality of primers (and subsequently into DNA or RNA target) within a single droplet may be different. Designing barcodes is shown U.S. Pat. No. 6,235,475, the contents of which are incorporated by reference herein in their entirety. In certain embodiments, the barcode sequences range from about 2 nucleotides to about 25 nucleotides, e.g., about 5 nucleotides to about 10 nucleotides. Since the barcode sequence is sequenced along with the template nucleic acid to which it is attached, the oligonucleotide length should be of minimal length so as to permit the longest read from the template nucleic acid attached. Generally, the barcode sequences are spaced from the template nucleic acid molecule by at least one base (minimizes homopolymeric combinations).

Methods of the invention include attaching the barcode sequences to a functional N-mer such as a primer, then incorporating the barcode into a target, or portion thereof using, for example, multiple displacement amplification. The labeled strands produced by MDA are able to be fragmented or sheared to desired length, e.g. generally from 100 to 500 bases or longer, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA before or after fragmentation.

Barcode Droplet Libraries

In certain embodiments, the invention provides libraries of barcodes in droplets, as well as methods of making and using them. Making a barcode library is shown in FIG. 2 through FIG. 5. A barcode droplet library generally is a set of droplets containing barcodes (e.g., unique N-mers) for incorporation into a target molecule. Barcodes can be provided in an oligonucleotide containing sequence to function as an amplification primer with the result that a nucleic acid subsequently introduced into the droplet will be amplified, and the copies that result will include the barcode of that droplet. However, barcodes can also be provided that are used to label proteins or other molecules of interest.

In various embodiments, there is a distinction between a droplet library that is used directly with samples (function N-mer is PCR primer, random hexamer, etc), and a library that can be used either for continued building of higher complexity composite barcodes, or directly with samples that have been prepared to contain appropriate sticky-ends (functional N-mer is a sticky end; the haplotyping with annealed samples is one example of this case).

Regardless of the library type, the functional N-mer can be chosen based on a type of target material. For example, for barcoding antibodies, one set of antibodies could all have a sticky-end that binds one class of barcodes, and another antibody set would have a different sticky end, for example, to bind a capture tag. In another example, a set of barcoded PCR primers could include one forward/reverse pair that could bind to one class of barcodes and a different 'universal' forward/reverse pair that binds to a different class of barcodes (with the compliment to the second for/rev pair).

Figure 4:
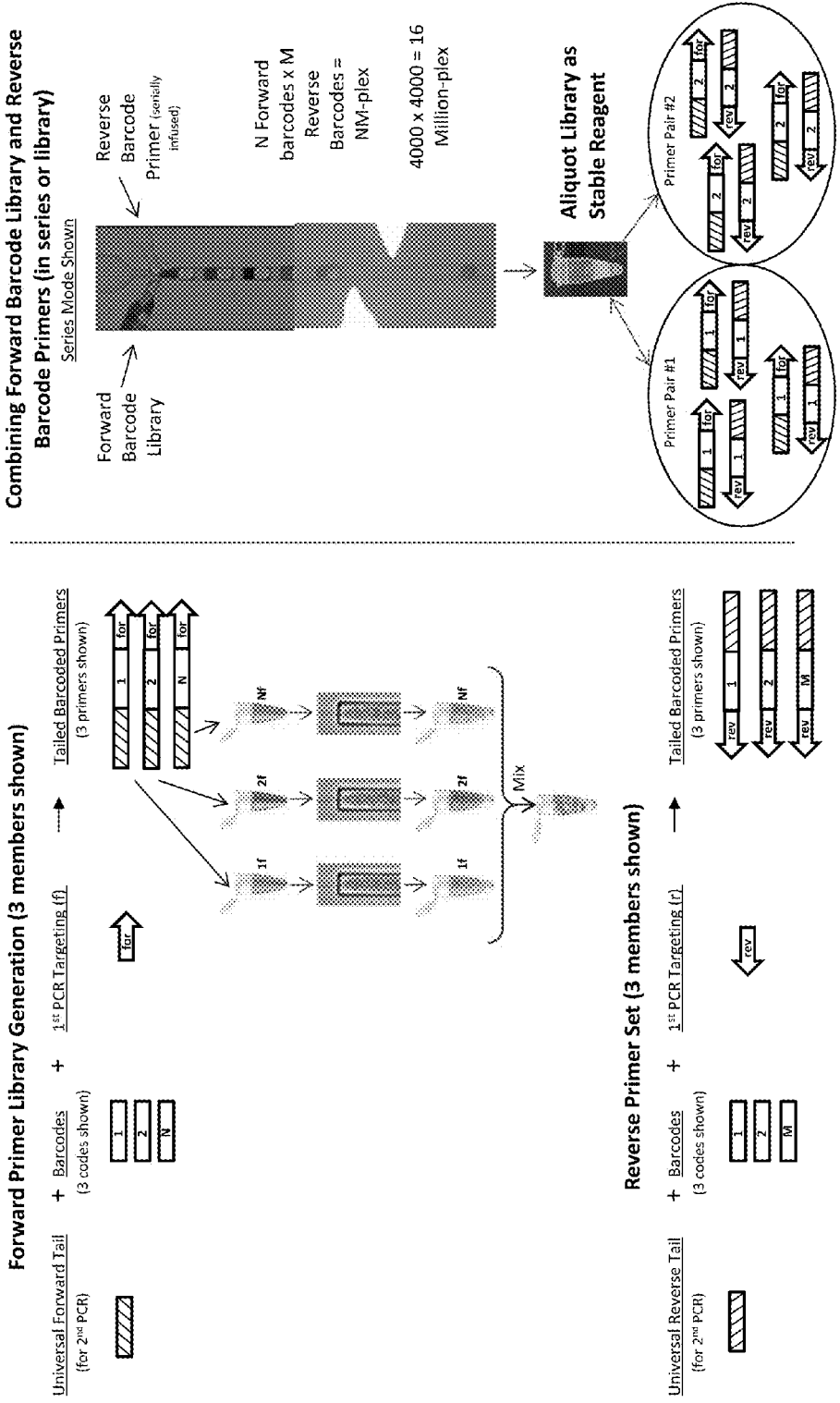
FIG. 4 shows a universal barcode droplet library with targeting primers.

Barcodes can be provided as oligonucleotides as discussed above. In certain embodiments, a barcode is provided as part of a tripartite construct (e.g., as shown in FIG. 4) including a universal priming site, a barcode, and a sequence specific region. The sequence specific region can provide a PCR primer of known sequence, a random hexamer for MDA, or any other suitable nucleotide sequence that will bind to target. In other embodiments, the invention provides universal barcode libraries (e.g., droplets that each contain a plurality of universal primers or priming sites all having a single unique barcode, but without a sequence-specific region). A universal barcode generally includes a unique N-mer and a sticky end.

For creation of a library, a number of different barcodes will be obtained. For any given length, L, in nucleotides, the number N of unique barcodes that can be made using standard nucleotides (A, T, C, G) is given by $N=4^L$. It can be seen by simple calculation, for example, that if barcodes are to be five nucleotides long, then 1,024 unique barcodes are possible. Six, seven, and eight nucleotides in a barcode allow for 4096, 16384, and 65536 unique barcodes, respectively. If each barcode includes 10 nucleotides, then more than one million unique libraries can be made. At 15 nucleotides, then N is greater than one billion. Combining such barcodes using sticky ends (shown in FIG. 2) gives $N'=N\times N$. In creating a barcode droplet library, a number of droplets are formed, each preferably containing copies of a uniquely-barcoded construct.

For embodiments in which primer pairs are used, for example, where target nucleic acid is to be amplified using PCR, one step of creating a barcode droplet library involves creating a forward library. In a tripartite construct-based embodiment, each droplet in the forward library will contain a plurality of copies of uniquely-barcoded tripartite "forward" primers. That is, each tripartite construct in the forward library will comprise 5'-universal forward tail-barcode-forward primer-3'. While any number of droplets can be made in the forward library, in a preferred embodiment, the forward library contains sets that include a number of droplets equal to or less than the number of possible unique barcode given the number of nucleotides in each barcode. Thus, if a six nucleotide barcode is to be used, sets of approximately 4,000 droplets (or any arbitrarily-lower number) can be made.

A corresponding number of reverse tripartite constructs can be made (e.g., universal reverse tail-barcode-reverse primer). Then, microfluidic methods and devices as discussed herein can be used to add reverse constructs to each droplet containing forward constructs. Forward and reverse constructs can be put into droplets together in a variety of ways. For example, the forward and reverse constructs can be put into droplets a single well at a time. In some embodiments, flowing microfluidic systems are used. For example, a stream containing reverse constructs can be merged with a stream containing the forward droplets. As each droplet passes the merge point, the reverse construct is added.

Forward and reverse constructs can be put together randomly, or they can be put together in a serial fashion. In a serial approach, the first reverse construct can be added to all droplets (e.g., about 4,000) of a set of forward droplets by flowing those droplets through the merge point. Then, the second reverse construct can be used, and the steps repeated. A second complete set of forward droplets can be streamed into the second reverse construct, thereby creating 4,000 droplets, each of which contains a unique forward primer and the second reverse primer construct. After this process is repeated 4,000 times, 4,000×4,000 droplets will have been made, each containing uniquely-barcoded primer pairs (e.g., as tripartite constructs). Production of a large barcode library by these means need not include tripartite constructs and can use any constructs that include barcodes (e.g., primer pairs+barcodes; random hexamers+barcodes; universal primers+barcodes; etc.).

Where primer pairs are used, any number of primers or primer pairs can be used. Where a large number of cells will be assayed for information about a single locus of interest, a single PCR primer pair may be used in a large barcode droplet library. Where a barcode droplet library will be used to assay a number X of loci on a plurality of genomes, X primer pairs will be used. Where MDA will be used to amplify one or more target regions, a number of random hexamers will be used according to calculations discussed elsewhere.

In certain embodiments, only one type of construct is provided per droplet (i.e., forward only or reverse only, without a corresponding reverse). Thus, methods of the invention include preparation of barcode droplet libraries in which each droplet contains a single barcoded construct without a corresponding partner-pair barcode.

In certain embodiments, primers for an initial round of amplification are universal primers, for example, where the target to be amplified includes universal priming sites.

As discussed elsewhere herein, droplets of the invention are stable when stored. Thus a barcode droplet library can be prepared having any arbitrarily large size and stored to be later used in any of the suited assays described herein or known in the art.

In some embodiments, the invention provides methods involving a two-step "drop" PCR wherein multiple sets of primers are provided in a droplet. Either, both, or neither set of primers can include barcodes. Target material is added to the droplet. A first round of amplification is performed, and then a condition is changed, and amplification is performed again. For example, low-stringency conditions are created for the first amplification, through manipulation of temperature or chemical environment. Thus, even though other primers are present, an intended first set of primers outcompetes or predominates in amplification. By these means, target nucleic acid can be amplified and barcoded in multiple steps.

As discussed above, a barcode library generally includes constructs having a functional N-mer and a unique N-mer. In some embodiments, a functional N-mer is a sticky end.

The invention provides methods and materials to generate large, complex, or extensible barcode libraries, and applications for barcode libraries.

In order to facilitate generation of a sufficiently high number of barcoding oligonucleotide species for labeling a wide range of molecules, particles, or cells, one can generate a "Universal Barcoding Droplet Library" for combining with samples. This reagent can be used to barcode DNA, RNA, proteins, chemicals, beads or other species present in the sample if they contain complimentary binding moieties.

The concepts for generation and use of a droplet library for massively parallel molecular barcoding apply to all forms of binding agents that can have a readable identifying barcode appended. Expanded 'plex' for barcode identifiers is provided via the use of barcodes in droplets, such that one barcode can be linked to other barcodes via one or more library combinations, resulting in multiplicatively larger sets of unique barcodes.

In certain embodiments, antibodies or oligonucleotides are used as functional N-mers for binding to sample molecules with (optionally releasable) unique N-mers as barcodes. Both the types and numbers of each type of barcodes are determined by a digitally quantified readout, and thus correlated with the presence and concentration of various biomarker species in a sample.

Two basic types of universal barcoding droplet libraries are described as examples of the general concept for providing a means to append unique barcodes to target material for identification or quantification, but the concept is not limited to these examples and at least one example will be given where the two described library types are used together.

Figure 3:
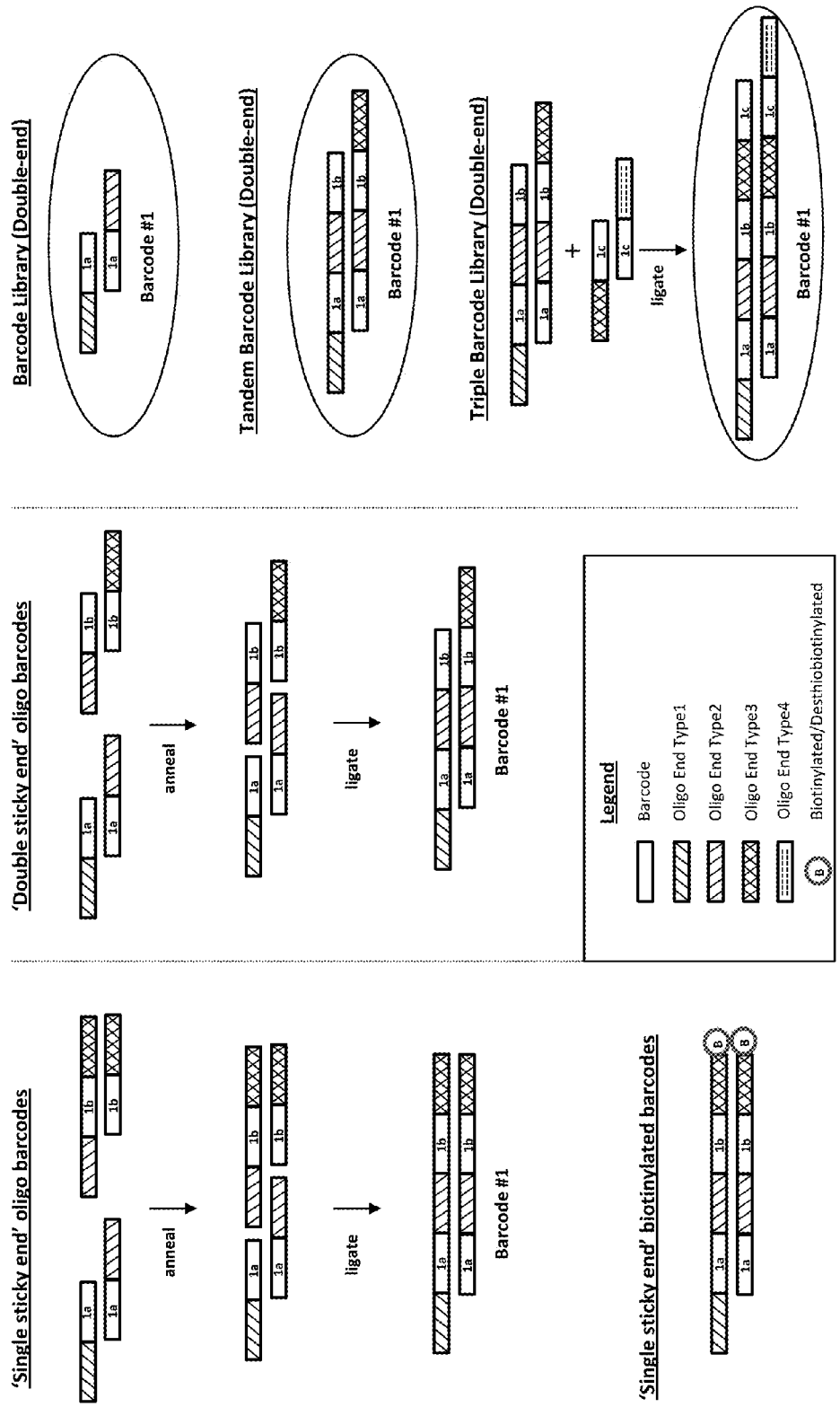
FIG. 3 shows six types of barcodes with sticky end components.

In the first set of examples, a universal binding barcode droplet library is described for use in a 'bind and ligate' approach (see FIG. 3). This library type consists of droplets containing oligonucleotide strands that encode barcodes and contain ligation competent ends, enabling the modular linking of barcodes by specific hybridization (also referred to as 'annealing' or 'binding') in droplets followed by ligation into a covalently bonded strand (or duplex) of bases. The Universal Binding Barcode Droplet Library can be used directly with samples that contain pre-bound barcoded binding moieties, as a 'primary' library that is combined with binding moieties targeting specific sample molecules, or can be used in the construction of 'secondary' or higher order binding barcode libraries through the successive combination of droplet libraries. The end use of such libraries can include assembly of the barcoded specific binding agents into a release-able and readable single molecule for use in digital quantification of bound targets for a variety of applications.

In the second set of examples, a universal priming barcode droplet library is described for use in a 'bind and prime' approach. FIG. 4 shows one example of a universal barcode droplet library with targeting primers (e.g., to "bind and prime"). This library type consists of droplets containing barcoded primers for PCR (or other polymerase) priming, such that after combination with a sample droplet containing at least one target sequence from the same single DNA or RNA molecule, or multiple molecules co-localized in a single droplet, a digitally readable oligonucleotide barcode is attached to the target molecule's sequence. Since all polymerase generated molecules in the same droplet will have the same barcode, the co-localization information is retained after release from the droplet, and any sequencer can be used to both determine the sequence and count the number of templates traceable to each original droplet.

Figure 9:
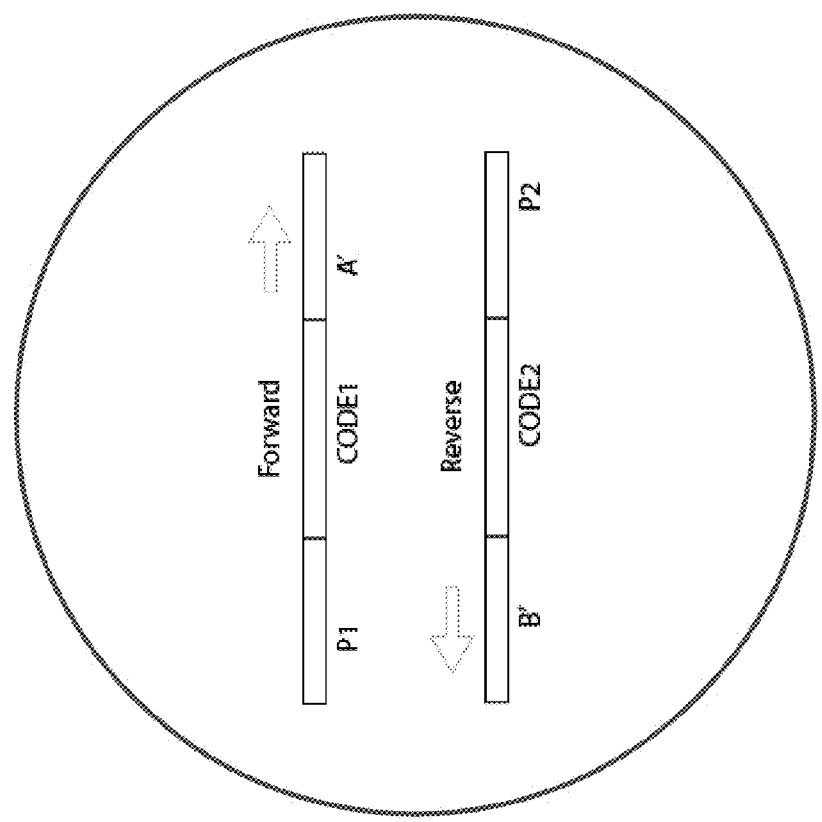
FIG. 9 show an example of a droplet library of primer pairs. Each primer pair includes a coding portion and a portion that hybridizes to the adaptors attached to the smaller fragments. Each pair may also optionally include a universal primer site.

Both library types enable molecular barcoding in droplets, providing a large excess of unique identifying barcodes compared to the number of sample droplets, or compared to the number of sample objects or molecules contained in the droplets, thus allowing digital quantification of many targets of interest on various reading platforms. Significantly, the two types are not exclusive of each other. For example, FIG. 9 shows ligating sticky-ended universal barcodes to barcoded PCR primers.

Sticky End Libraries

Figure 5:
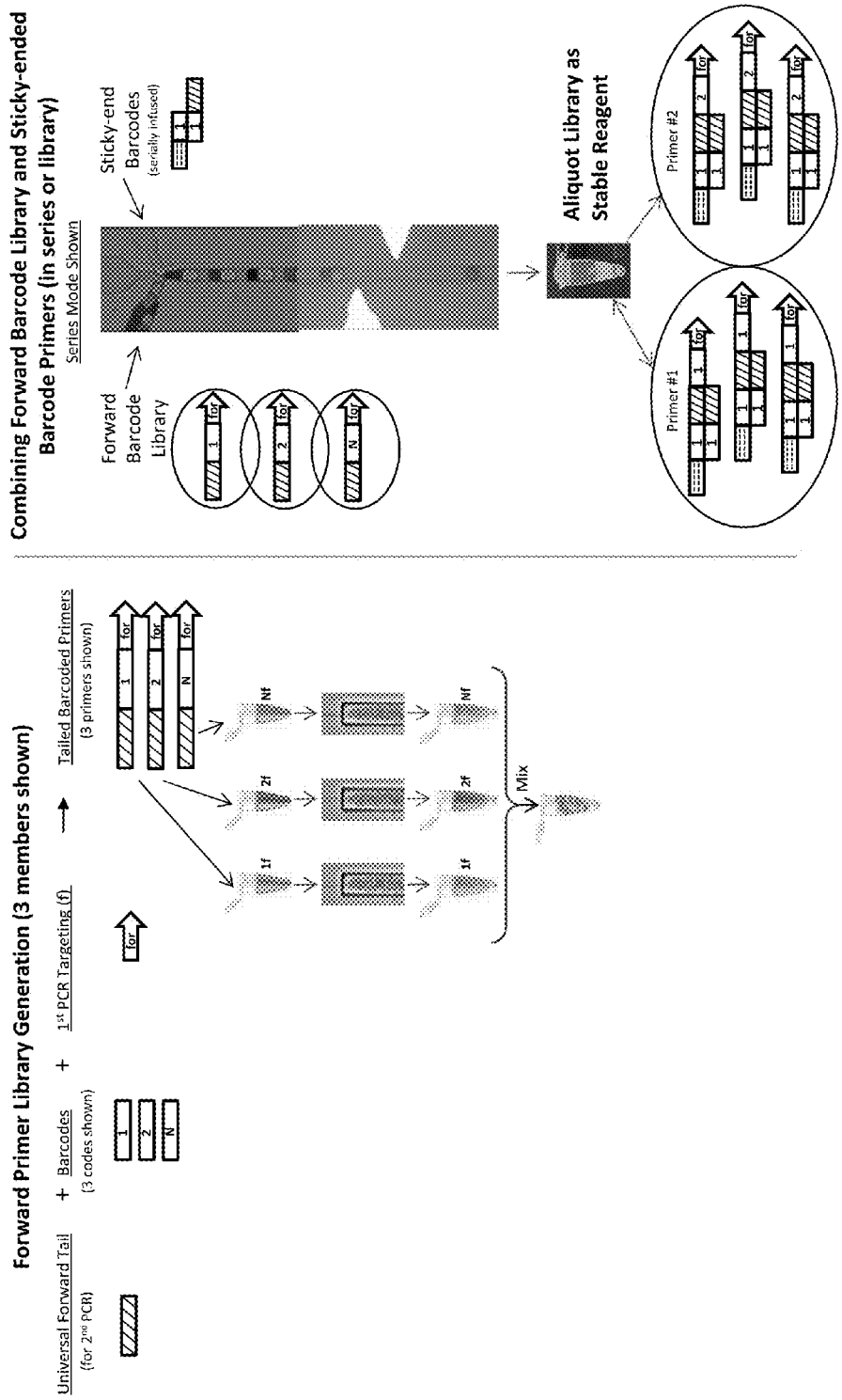
FIG. 5 shows a universal barcode droplet library.

FIG. 5 shows the overall scheme for construction of a universal binding barcode droplet library. Pairs of overhanging complimentary oligonucleotide barcodes are chemically synthesized (using standard commercial manufacturing methods) such that the complementary barcoding sequences are flanked by 'sticky-ends' for subsequent annealing and ligation to the target species or other barcodes, or for polymerase or other enzymatic priming. The oligonucleotides may include 5-prime or 3-prime phosphorylation, or combinations of these or other modifications. Methods to make oligonucleotides resistant to nuclease activity may be used, including the use of 2'0-Methyl RNA bases and/or phosphorothioated bonds to form the entire backbone of the oligo or to cap the ends of the sequence. PNA, LNA, or other modified nucleotide structures can also be used. A sticky-end may be any length and sequence, with preferred embodiments containing base pairs including restriction endonuclease cleavage sites, or priming sites for sequencing or digital PCR, or an-ay hybridization, and any number of sticky-ends with different sequences can be utilized. Sticky-end sequences may be used as barcode identifiers as part of composite barcodes.

Figure 2:
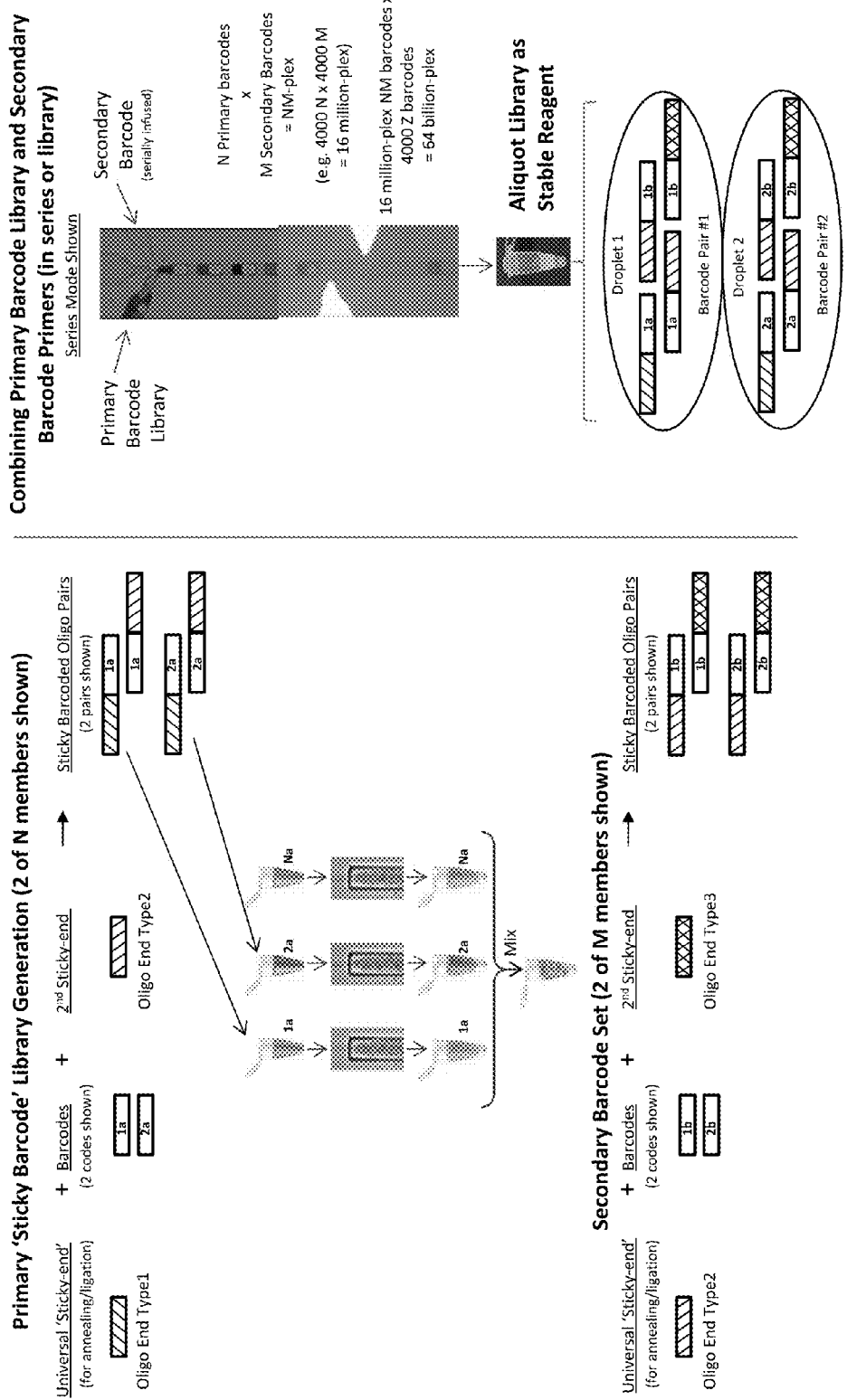
FIG. 2 shows a method of making a universal barcode library.

Two example barcoded oligonucleotide pairs are shown in FIG. 2 (1a and 2a, flanked by sticky-end Type 1 and sticky-end Type 2). To construct a droplet library each discrete complementary oligonucleotide pair can be placed together into a standard microtiter-plate well and formed into droplets, which can be subsequently mixed with other oligonucleotide pair-containing droplets to make a 'primary barcode droplet library'. Forming droplets for a library is discussed in U.S. Pub. 2010/0022414. The number of pair types (N members) is not limited.

These storable stable droplets can either be used directly as an N-member barcoding library, or combined with another barcoding oligonucleotide set (M-members) to form a 'tandem' barcoded library with N×M=NM-plex. A 4000 N-member library combined with a 4000 M-member library will generate a 16 million-plex barcode library.

Combination of the N-member primary barcode library with the M secondary barcodes can be done in series (with each member of the M-barcode combined as an aqueous liquid one at a time with the N-member primary barcode library, using various methods including lambda or pico-injection modes and co-flow) or by combining the N-member and M-member library droplets in parallel (primary library combined with secondary library).

Heterogeneous mixtures of barcodes (e.g. barcodes synthesized using degenerate bases) can be converted into a unique set of droplet barcodes by addition of a unique sticky-end. Manipulation of droplets is described in U.S. Pat. No. 7,718,578 and U.S. Pub. 2011/0000560.

By combining complimentary sticky-ends from two barcode sets, the four oligonucleotide types present in the final combined droplet will specifically hybridize to create a sticky-ended tandem barcode (e.g., droplet 1 or 2 in FIG. 2). This can then be ligated together. A similar specific hybridization will occur for additional numbers of barcodes containing complimentary sticky-ends. This is illustrated in FIG. 3, with 'single sticky-ended' barcoded oligonucleotide pairs shown on the left, where one end is capped such that there is no overhang, and 'double sticky-ended' barcode oligonucleotides shown in the middle panel (either different or similar sticky-ends can be used, with different ends precluding promiscuous concatamer formation). Additional modifications of the sticky-ends can also be included (e.g. biotin or desthiobiotin, shown on the bottom left of the figure).

After annealing the sticky ends together, adjacent strands can be ligated together.

The panel on the right of FIG. 3 shows the initial binding barcode droplet library (only one droplet and one molecule of each type shown, with a barcode identifier 1a) on the top, a tandem barcoded droplet library formed by combination of a primary barcode and a secondary barcode in the middle (e.g. barcode identifier 1a:1b), and a triple barcoded library at the bottom (formed by combining a secondary barcoded library with a third barcode, resulting in barcode identifier 1a:1b:1c).

This modular construction is not limited to the combinations shown, with any composite sticky-ended barcode library able to be combined with additional barcodes in subsequent rounds of droplet combination. Even a low number of combinations can result in a very high level of barcode-plex.

Figure 6:
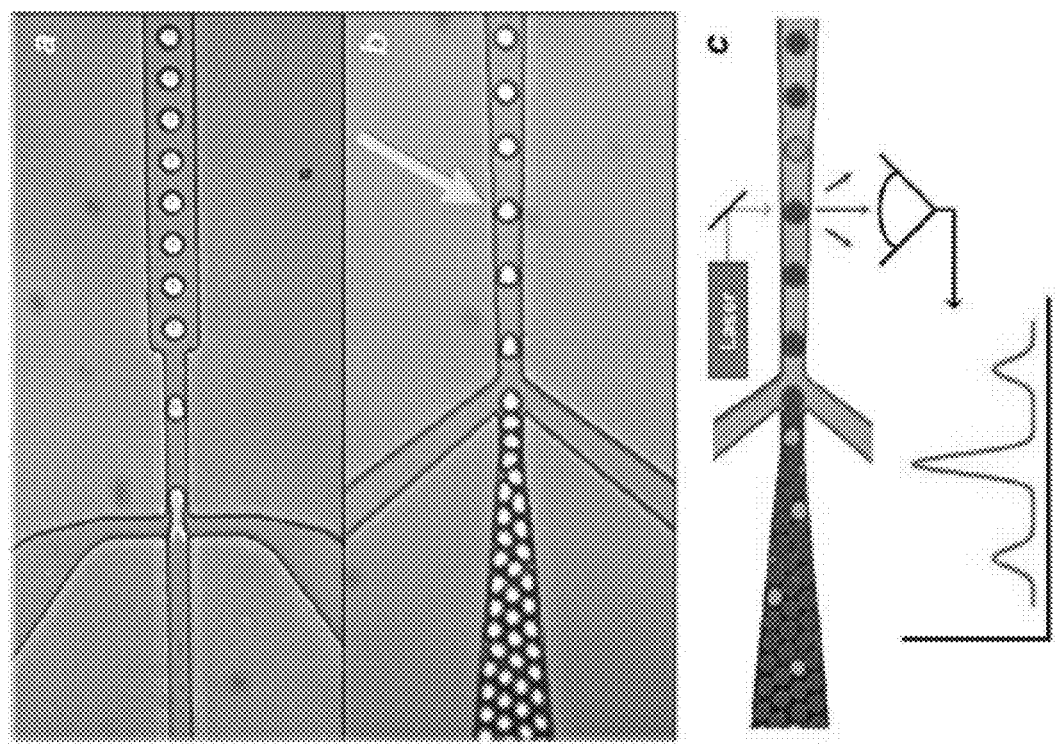
FIG. 6A shows a droplet generation chip.
FIG. 6B depicts the droplet spacing for readout.
FIG. 6C depicts a cartoon of droplet readout by fluorescence.
Figure 7:
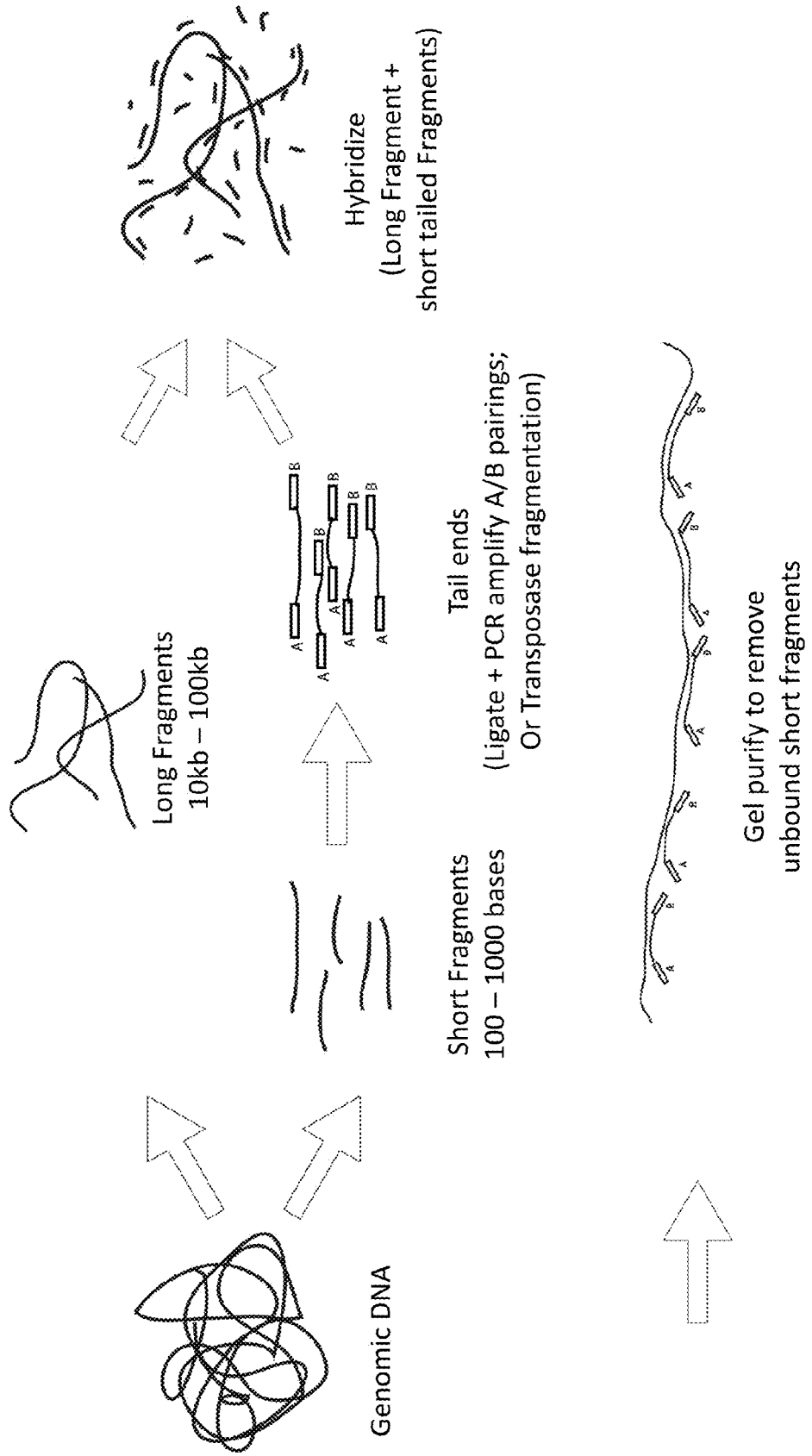
FIG. 7 shows an overview of an embodiment of methods of the invention. This figure shows fragmenting a portion of genomic DNA to produce small DNA fragments while the remaining portion is subjected to a light fragmenting to produce longer fragments (e.g. 10-1000 kb). A and B adapters are attached to each of the small fragments and the smaller fragments are allowed to hybridize to the longer fragments, producing a longer fragment having smaller fragments tiled along its length. In this embodiment, a gel purification step is performed to remove unbound smaller fragments.
Figure 8:
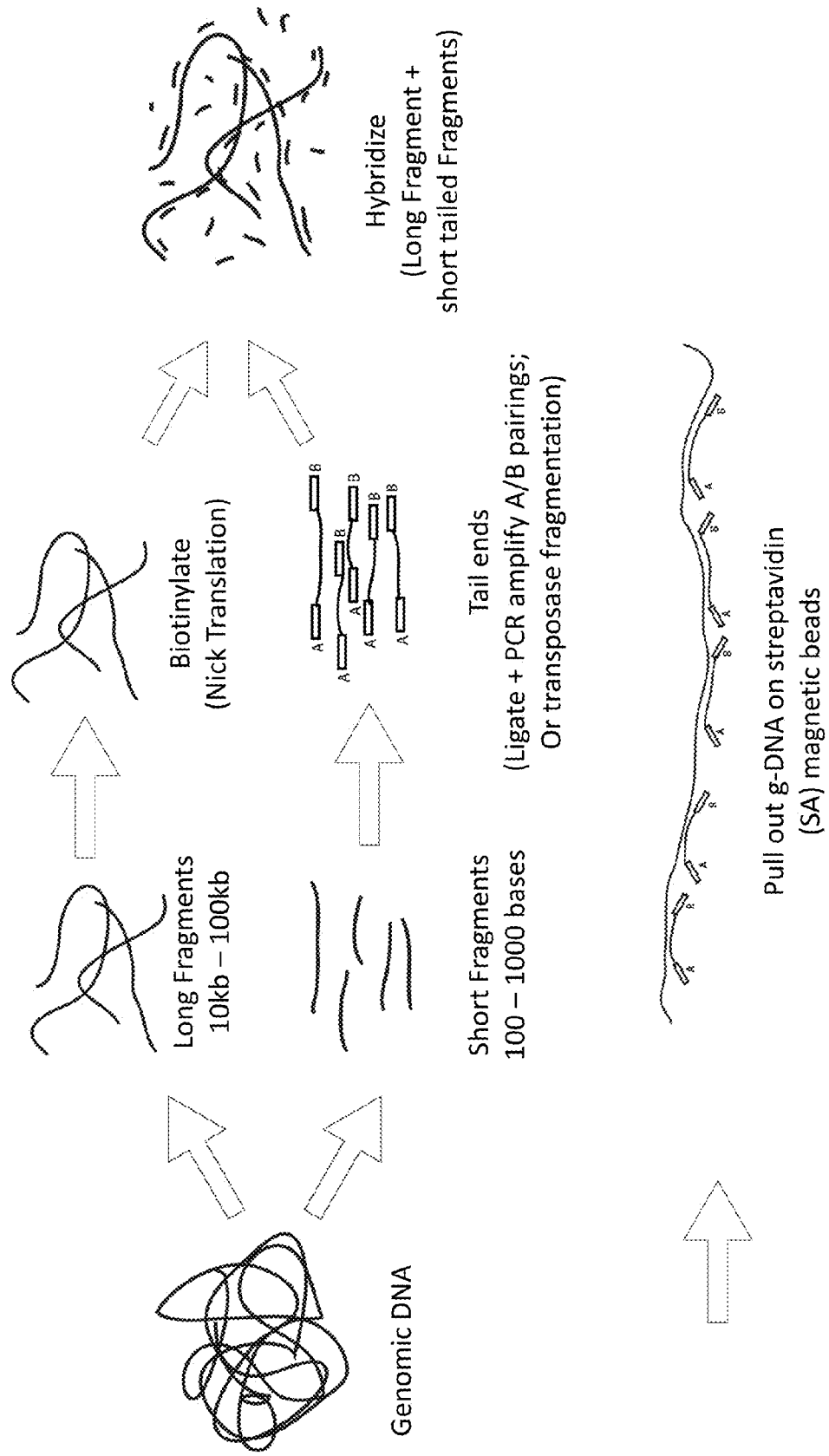
FIG. 8 shows an overview of another embodiment of methods of the invention. This figure shows fragmenting a portion of genomic DNA to produce small DNA fragments while the remaining portion is subjected to a light fragmenting to produce longer fragments (e.g. 10-1000 kb). A and B adapters are attached to each of the small fragments. The longer fragments are biotinylated. The smaller fragments are allowed to hybridize to the longer fragments, producing a longer fragment having smaller fragments tiled along its length. In this embodiment, the biotinylated longer fragments having smaller fragments bound thereto are then bound to streptavidinated beads, so that they can be separated from unbound smaller fragments.

For example, a 16 million-plex tandem barcode library (made from 4000 N×4000 M barcoded oligos) can be combined with another sticky-ended set of 4000 Z barcoded oligos to form a 64 billion-plex barcode library (16 million NM members×4000 Z-members=64 billion). As shown in FIG. 6, the oligonucleotides can be designed such that the resulting annealed oligo set can have a single or double sticky-ends (with different or similar ends).

A barcode library can also be made to include a sticky-end adapter specific for a sequencing platform. In certain embodiments, a construct is made that includes a sequencing platform N-mer and a sticky-end N-mer. A library of these constructs can be made. Separately, a universal barcode library as discussed above can be made. The, the universal barcode library can be combined with the sequencing platform adapter library by means of the sticky ends in view of a particular application. Thus products of any analysis discussed herein can be adapted to go directly into the workflow of any given sequencing platform (e.g. sticky-ended Illumina adaptors to anneal/ligate onto either the primer library or the output from a targeted sequencing run, so that it could be hybridized directly onto their flow cell. A different sticky-end adaptor set could be used for 454, etc.). This approach can minimize PCR bias.

A universal PCR primer barcode library can also be prepared with an unlimited amount of plex by creating sticky-ended forward and reverse primers that can be further combined with additional numbers of sticky-ended barcodes to generate combinatorial barcodes. The forward and reverse universal primers are constructed in an identical fashion as described above and in FIG. 4 (primary barcoded primers) and then annealed to a sticky-ended barcode oligonucleotide pair (either single or double sticky-ended as shown in FIG. 2) and subsequently ligated, to make a contiguous forward (and/or reverse) primer annealed to the complimentary oligo that was used to anneal to the primary barcoded primer.

Sequencing

Having labeled the DNA, RNA, or protein of cell-free material, a collection of cells, single cell, or portion thereof, using the methods described herein, the labeled (and possibly amplified) sample may be sequenced. Sequencing can be carried out using any suitable sequencing technique. A particularly useful method for nucleic acid sequencing is one wherein nucleotides are added successively to a free 3' hydroxyl group, resulting in synthesis of a polynucleotide chain in the 5' to 3' direction. The nature of the nucleotide added may be determined after each nucleotide addition or at the end of the sequencing process. Sequencing techniques using sequencing by ligation, wherein not every contiguous base is sequenced, and techniques such as massively parallel signature sequencing (MPSS) where bases are removed from, rather than added to the strands on the surface are also within the scope of the invention.

The invention also encompasses methods of sequencing amplified nucleic acids generated by solid-phase amplification. Thus, the invention provides a method of nucleic acid sequencing comprising amplifying a pool of nucleic acid templates using solid-phase amplification and carrying out a nucleic acid sequencing reaction to determine the sequence of the whole or a part of at least one amplified nucleic acid strand produced in the solid-phase amplification reaction. The initiation point for the sequencing reaction may be provided by annealing of a sequencing primer to a product of a solid-phase amplification reaction. In this connection, one or both of the adaptors added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilized on the solid surface are so-called bridged structures formed by annealing of pairs of immobilized polynucleotide strands and immobilized complementary strands, both strands being attached to the solid support at the 5' end. Arrays comprised of such bridged structures provide inefficient templates for typical nucleic acid sequencing techniques, since hybridization of a conventional sequencing primer to one of the immobilized strands is not favored compared to annealing of this strand to its immobilized complementary strand under standard conditions for hybridization.

In order to provide more suitable templates for nucleic acid sequencing, it may be advantageous to remove or displace substantially all or at least a portion of one of the immobilized strands in the bridged structure in order to generate a template which is at least partially single-stranded. The portion of the template which is single-stranded will thus be available for hybridization to a sequencing primer. The process of removing all or a portion of one immobilized strand in a 'bridged' double-stranded nucleic acid structure may be referred to herein as linearization, and is described in further detail in U.S. Pub. 2009/0118128, the contents of which are incorporated herein by reference in their entirety.

Bridged template structures may be linearized by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, part number M55055), or by exposure to heat or alkali, cleavage of ribonucleotides incorporated into amplification products otherwise comprised of deoxyribonucleotides, photochemical cleavage or cleavage of a peptide linker Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., supra; Ausubel et al. supra). Denaturation results in the production of a sequencing template which is partially or substantially single-stranded. A sequencing reaction may then be initiated by hybridization of a sequencing primer to the single-stranded portion of the template.

Thus, the invention encompasses methods wherein the nucleic acid sequencing reaction comprises hybridizing a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One sequencing method which can be used in accordance with the invention relies on the use of modified nucleotides having removable 3' blocks, for example as described in WO04018497, US 2007/0166705A1 and U.S. Pat. No. 7,057,026, the contents of which are incorporated herein by reference in their entirety. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides, it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may be labeled (e.g., fluorescent label) for detection. Each nucleotide type may thus carry a different fluorescent label, for example, as described in U.S. Pub. 2010/0009353, the contents of which are incorporated herein by reference in their entirety. The detectable label need not, however, be a fluorescent label. Any label can be used which allows the detection of an incorporated nucleotide.

One method for detecting fluorescently labeled nucleotides comprises using laser light of a wavelength specific for the labeled nucleotides, or the use of other suitable sources of illumination. The fluorescence from the label on the nucleotide may be detected by a CCD camera or other suitable detection means. Suitable instrumentation for recording images of clustered arrays is described in WO07123744 and U.S. Pub. 2010/0111768, the contents of which are incorporated herein by reference in their entirety.

In all cases, regardless of the incorporation of molecular barcodes or the location of the barcodes in the event that they are incorporated, sequencing adaptors can be attached to the nucleic acid product in a bi-directional way such that in the same sequencing run there will be sequencing reads from both the 5' and 3' end of the target sequence. In some cases it is advantage to use the location of the barcode on the 5' or 3' end of the target sequence to indicate the direction of the read. It is well known to one skilled in the art how to attach the sequencing adaptors using techniques such as PCR or ligation.

The invention is not intended to be limited to use of the sequencing method outlined above, as essentially any sequencing methodology which relies on successive incorporation of nucleotides into a polynucleotide chain can be used. Suitable alternative techniques include, for example, the genome sequencers from Roche/454 Life Sciences (Margulies et al. (2005) Nature, 437:376-380; U.S. Pat. Nos. 6,274, 320; 6,258,568; 6,210,891), the SOLiD system from Life Technologies Applied Biosystems (Grand Island, N.Y.), the HELISCOPE system from Helicos Biosciences (Cambridge, Mass.) (see, e.g., U.S. Pub. 2007/0070349), and the Ion sequencers from Life Technologies Ion Torrent, Ion Torrent Systems, Inc. (Guilford, Conn.).

III. Probe-Type Labels

In addition to barcode-based methods discussed above, labeled target material can be analyzed using digital PCR methods or by counting of fluorescent probe labels. Digital PCR is discussed below. Methods further include incorporating labels having a fluorescent or other colorimetric probe using the methods described herein. In some embodiments, labels are incorporated and amplified material is released from encapsulation and can be input into a digital PCR reaction to simultaneously screen for multiple genotypes and/or mutations for a plurality of target genes in the sample.

Ideally, the sensitivity of digital PCR is limited only by the number of independent amplifications that can be analyzed, which has motivated the development of several ultra-high throughput miniaturized methods allowing millions of single molecule PCR reactions to be performed in parallel (discussed in detail elsewhere). In a preferred embodiment of the invention, digital PCR is performed in aqueous droplets separated by oil using a microfluidics system. In another preferred embodiment, the oil is a fluorinated oil such as the Fluorinert oils (3M). In a still more preferred embodiment the fluorinated oil contains a surfactant, such as PFPE-PEG-PFPE triblock copolymer, to stabilize the droplets against coalescence during the amplification step or at any point where they contact each other. Microfluidic approaches allow the rapid generation of large numbers (e.g. $10^6$ or greater) of very uniformly sized droplets that function as picoliter volume reaction vessels (see reviews of droplet-based microfluidics). But as will be described, the invention is not limited to dPCR performed in water-in-oil emulsions, but rather is general to all methods of reaction compartmentalization for dPCR. In the description that follows, the invention is described in terms of the use of droplets for compartmentalization, but it is understood that this choice of description is not limiting for the invention, and that all of the methods of the invention are compatible with all other methods of reaction compartmentalization for dPCR. In yet another embodiment, the labeled, amplified genetic mixture is analyzed using an array (e.g., microarray) readout.

Methods of the invention involve novel strategies for performing multiple different amplification reactions on the same sample simultaneously to quantify the abundance of multiple different DNA targets, commonly known to those familiar with the art as "multiplexing". Methods of the invention for multiplexing dPCR assays promise greater plexity— the number of simultaneous reactions—than possible with existing qPCR or dPCR techniques. It is based on the singular nature of amplifications at terminal or limiting dilution that arises because most often only a single target allele is ever present in any one droplet even when multiple primers/probes targeting different alleles are present. This alleviates the complications that otherwise plague simultaneous competing reactions, such as varying arrival time into the exponential stage and unintended interactions between primers.

In one aspect, the invention provides materials and methods for improving amplicon yield while maintaining the quality of droplet-based digital PCR. More specifically, the invention provides droplets containing a single nucleic acid template and multiplexed PCR primers and methods for detecting a plurality of targets in a biological sample by forming such droplets and amplifying the nucleic acid templates using droplet-based digital PCR.

Reactions within microfluidic droplets yield very uniform fluorescence intensity at the end point, and ultimately the intensity depends on the efficiency of probe hydrolysis. Thus, in another aspect of the methods of the invention, different reactions with different efficiencies can be discriminated on the basis of end point fluorescence intensity alone even if they have the same color. Furthermore, in another method of the invention, the efficiencies can be tuned simply by adjusting the probe concentration, resulting in an easy-to-use and general purpose method for multiplexing. In one demonstration of the invention, a 5-plex TaqMan® dPCR assay worked "right out of the box", in contrast to lengthy optimizations that typify qPCR multiplexing to this degree. In another aspect of the invention, adding multiple colors increases the number of possible reactions geometrically, rather than linearly as with qPCR, because individual reactions can be labeled with multiple fluorophores. As an example, two fluorophores (VIC and FAM) were used to distinguish five different reactions in one implementation of the invention.

Detection

In certain embodiments, after amplification, droplets are flowed to a detection module for detection of amplification products. For embodiments in which the droplets are thermally cycled off-chip, the droplets require re-injection into either a second fluidic circuit for read-out—that may or may not reside on the same chip as the fluidic circuit or circuits for droplet generation—or in certain embodiments the droplets may be re-injected for read-out back into the original fluidic circuit used for droplet generation. The droplets may be individually analyzed and detected using any methods known in the art, such as detecting the presence or amount of a reporter.

An apparatus can include optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Detecting labeled material in droplets is discussed in U.S. Pub. 2008/0014589; U.S. Pub. 2008/0003142, and U.S. Pub. 2010/0137163.

In certain aspects, the droplets of the invention contain a plurality of detectable probes that hybridize to amplicons produced in the droplets. Members of the plurality of probes can each include the same detectable label, or a different detectable label. The plurality of probes can also include one or more groups of probes at varying concentration. The groups of probes at varying concentrations can include the same detectable label which vary in intensity, due to varying probe concentrations.

In a separate embodiment the detection can occur by the scanning of droplets confined to a monolayer in a storage device that is transparent to the wavelengths or method or detection. Droplets stored in this fashion can be scanned either by the movement of the storage device by the scanner or the movement of the scanner over the storage device.

The invention is not limited to the TaqMan assay, as described above, but rather the invention encompasses the use of all fluorogenic DNA hybridization probes, such as molecular beacons, Solaris probes, scorpion probes, and any other probes that function by sequence specific recognition of target DNA by hybridization and result in increased fluorescence on amplification of the target sequence.

Optical Labels

In particular embodiments, the labels incorporated into the DNA or RNA of a single cell, or portion thereof, are optically labeled probes, such as fluorescently labeled probes that are attached to a primer (or N-mer) that hybridizes to a unique region of the target. Examples of fluorescent labels include, but are not limited to, Atto dyes, 4-acetamido-4'-isothiocyanatostilbene-2,2' disulfonic acid; acridine and derivatives: acridine, acridine isothiocyanate; 5-(2'-aminoethypaminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogalloHsulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline;

Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine/242 (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are FAM and VICTM (from Applied Biosystems). Labels other than fluorescent labels are contemplated by the invention, including other optically-detectable labels.

In a particular embodiment, the optical label can be conjugated to an antibody, an siRNA, an aptamer, or a ribozyme specific for target gene or region of interest on the target.

Labels can be used for identification of the library elements of the various types of droplet libraries. Libraries can be labeled for unique identification of each library element by any means known in the art. The label can be an optical label, an enzymatic label or a radioactive label. The label can be any detectable label, e.g., a protein, a DNA tag, a dye, a quantum dot or a radio frequency identification tag, or combinations thereof. Preferably the label is an optical label.

The label can be detected by any means known in the art. Preferably, the label is detected by fluorescence polarization, fluorescence intensity, fluorescence lifetime, fluorescence energy transfer, pH, ionic content, temperature or combinations thereof. Various labels and means for detection are described in greater detail herein.

Specifically, after a label is added to each of the various library elements, the elements are then encapsulated and each of the droplets contains a unique label so that the library elements may be identified. In one example, by using various combinations of labels and detection methods, it is possible to use two different colors with different intensities or to use a single color at a different intensity and different florescence anisotropy.

Quality Control

Optical labels are also utilized in quality control in order to ensure that the droplet libraries are well controlled, and that equal number of each library elements are contained within uniform volumes in each droplet library. After 120 minutes of mixing, using 8-labels in a 96-member library, the average number of droplets is 13,883 for each of the library elements.

In some quality control examples, 384-member libraries were prepared with eight optical labels; typically 5 to 20 micro-liters of each library element are emulsified into approximately 10 picoliter volume droplets so there are about 1 million droplets of each library element and 384 million droplets in the library.

The eight optical labels are a dye at concentrations that increase by a factor of c (where c ranges from about 1.2 to 1.4) from one optical label to the next so that the nth optical label has $(c)(n-1)$ the dye concentration of the lowest concentration. Optical labels are used with concentrations between 10 nM and 1 uM. Typically, the range of optical label concentrations for one series of labels is 1 order of magnitude (e.g., 10 nM to 100 nM with a multiplier of 1.43 for each increasing label concentration). A larger range of droplet label concentrations can also be used. Further, multiplexed two-color labels can be used as well.

Plates are prepared with 384 separate library elements in separate wells of the 384-well plates; 8 of which have optical labels. The library elements are made into droplets, collected in a vial, (also known as a creaming tower) and mixed for several hours. The mixer works by flipping the vial over about once every 30 seconds and then allowing the droplets to rise. Multiple plates can be emulsified and pooled or collected sequentially into the same vial.

A small fraction of the droplets are taken out of the vial to verify 1) that the droplets are present in the correct predetermined ratio and 2) that the droplets are of uniform size. Typically, 1,000 to 10,000 droplets of each library element (0.384 to 3.84 million QC-droplets) are removed from the vial through a PEEK line in the center opening in the vial cap by positive displacement with a drive oil infused through the side opening in vial cap. The PEEK line takes the droplets into a port on a microfluidic chip at a rate of several thousand droplets/second; for 10 picoliter droplets at a rate of 3000 droplets/s corresponds to a typical infusion rate of roughly 110 micro-liters/hr. Once on chip the droplets are spaced out by adding oil before they are imaged and pass one droplet at a time through a laser excitation spot. Maximum fluorescence intensity data from individual droplets is collected for all of the QC-droplets and histograms are built to show the number of droplets within a given fluorescence intensity range. As expected, if eight of the library elements have optical labels, then there are eight peaks in the histograms. The increasing concentration factor c=1.38 results in uniformly separated peaks across one decade when plotted on a log scale. The relative number of droplets in each peak is used as a quality metric to validate that the libraries were prepared with the expected relative representation. In this example, the percent variation is determined to be only 2.7% demonstrating that all library elements have uniform representation.

Image analysis can be utilized to determine and monitor osmotic pressure within the droplets. Osmotic pressure (e.g., two member library prepared with a small difference in buffer concentration) can effect droplets. Specifically, droplets with a lower salt concentration shrink over time and droplets with a higher salt concentration grow over time, until uniform salt concentrations are achieved.

Image analysis can also be utilized for quality control of the library reformatting process. After the various library elements are generated, pooled and mixed, optical labels can be used to verify uniform representation of all library elements. Additionally, image analysis is used to verify uniform volume for all droplets.

Further, image analysis can be used for shelf life testing by quantifying the materials performance. Droplets are stored in vials under a variety of conditions to test droplets stability against droplet-droplet coalescence events. Conditions tested include temperature, vibration, presence of air in vials, surfactant type, and surfactant concentration. A Quality Score of percent coalescence is calculated by image analysis. Shelf-life for the droplet libraries of the present invention exceed 90 days.

Droplet Digital PCR

In certain aspects, the invention provides methods and systems for droplet digital PCR including high plexity multiplexing.

An exemplary microfluidic system for droplet generation and readout is depicted in FIG. 6. The microfluidic system for droplet generation and readout. As shown in FIG. 6a (droplet generation chip), a continuous aqueous phase containing the PCR master mix, primers, and probes, and template DNA is flowed into the fluidic intersection from the left, and the carrier oil enters from the top and bottom. An emerging bolus of aqueous liquid is imaged inside the intersection just prior to snapping off into a discrete 4 pL droplet as the fluidic strain began to exceed the surface tension of the aqueous liquid. The steady train of droplets leaving the intersection toward the right is collected off chip as a stable emulsion for thermal cycling. FIG. 6b depicts the droplet spacing for readout. Flows are arranged as in FIG. 6a, except instead of a continuous phase, the emulsion from (a) is injected from the left into the intersection after thermal cycling. The oil drains from the emulsion during off-chip handling, hence the emulsion appears tightly packed in the image before the intersection. The oil introduced in the intersection separates the droplets and the fluorescence of each droplet is measured at the location marked by the arrow. FIG. 6c depicts a cartoon of droplet readout by fluorescence. The relatively infrequent PCR(+) droplets (light gray) flow along with the majority of PCR(−) droplets (dark gray) toward the detector. The droplets are interrogated sequentially by laser induced fluorescence while passing through the detection region.

In a serial dilution the average number of target DNA molecules per droplet—called the "occupancy" from this point forward—decreases in direct proportion to the DNA concentration. The occupancy is calculated from Poisson statistics using the following equation well known to those experienced in the art:

$$\text{occupancy} = \ln\left(\frac{P+N}{N}\right) \tag{1}$$

where P and N are the numbers of PCR(+) and PCR(−) droplets respectively.

Digital PCR performance in the emulsion format is validated by measuring a serial dilution of a reference gene, branched chain keto acid dehydrogenase E1 (BCKDHA). Mixtures of the PCR master mix, 1× primers and probe for BCKDHA, and varying concentrations of a mixture of human genomic DNA (1:1 NA14091 and NA13705) are compartmentalized into over one million 5.3 pL droplets in a water-in-fluorinated oil emulsion using the droplet generation microfluidic chip. The emulsion is thermally cycled off-chip and afterwards the fluorescence of each droplet is analyzed by fluorescence in the readout chip (see FIG. 48).

Droplets are analyzed by fluorescence while flowing through the readout chip to count the numbers of PCR(+) and PCR(−) droplets (see FIG. 48c). As each droplet passes the detection zone (marked with an arrow in FIG. 48b), a burst of fluorescence is observed. To account for small run-to-run differences in the fluorescence intensity that can occur due to different chip positioning, etc., each set of data is scaled such that the average fluorescence intensity of the empty droplets is 0.1 V.

Equivalents

The invention may be embodied in other specific forms without departing from the spirit or essential characteristics thereof. The foregoing embodiments are therefore to be considered in all respects illustrative rather than limiting on the invention described herein.

Incorporation by Reference

References and citations to other documents, such as patents, patent applications, patent publications, journals, books, papers, web contents, have been made throughout this disclosure. All such documents are hereby incorporated herein by reference in their entirety for all purposes.

What is claimed is:

1. A method for preparing nucleic acid for analysis, the method comprising the steps of:
   fragmenting nucleic acid molecules from a sample into long fragments comprising a length in a range of 5 kilobases-100 kilobases and short fragments comprising a length in a range of 100 bases-1000 bases;
   attaching an adaptor to each of 3' and 5' ends of the short fragments;
   hybridizing a plurality of the short fragments from the sample to individual long fragments from the sample to form a plurality of fragment complexes;
   compartmentalizing the fragment complexes in droplets with a primer pair species complementary to adaptors attached to the short fragments, wherein each droplet comprises one fragment complex and the primer pair species comprises a barcode; and
   amplifying the short fragments from the fragment complex in each droplet using the primer pair species.

2. The method according to claim 1, wherein removing comprises conducting a gel purification assay that separates the hybridized fragments from the unhybridized short fragments.

3. The method according to claim 1, wherein prior to the hybridizing step, the method further comprises attaching a first member of a binding pair to the long fragments.

4. The method according to claim 3, further comprising the step of removing unhybridized short fragments that comprises exposing the fragment complexes and the unhybridized short fragments to a solid support comprising a second member of the binding pair such that the fragment complexes bind to the solid support via the binding pair and are separated from the unhybridized short fragments that do not bind the support.

5. The method according to claim 4, wherein the binding pair is selected from the group consisting of: biotin/streptavidin; carbohydrate/lectin; and antibody/antigen.

6. The method according to claim 1, wherein compartmentalizing comprises:
   encapsulating the primer pair species into the droplets; and
   introducing the fragment complexes to the droplets.

7. The method according to claim 1, wherein the droplets comprise an aqueous fluid surrounded by an immiscible fluid.

8. The method according to claim 7, wherein compartmentalizing comprises partitioning the aqueous fluid as it is flowing through a channel with the immiscible fluid.

9. The method according to claim 8, wherein the immiscible fluid is oil.

10. The method according to claim 9, wherein the oil is a fluorinated oil.

11. The method according to claim 9, wherein the oil comprises a surfactant.

12. The method according to claim 11, wherein the surfactant is a fluorosurfactant.

13. The method according to claim 1, wherein compartmentalizing comprises merging the droplet that comprises the fragment complex with a droplet comprising the primer pair species.

14. The method according to claim 13, wherein merging occurs in the presence of an electric field.

15. The method according to claim 1, wherein compartmentalizing comprises merging a portion of a fluid stream comprising the fragment complex with a droplet comprising the barcoded primers.

16. The method according to claim 15, wherein merging occurs in the presence of an electric field.

17. The method according to claim 1, wherein amplifying is by polymerase chain reaction.

18. The method according to claim 1, further comprising sequencing the amplified short fragments and aligning obtained sequence reads.

19. The method according to claim 1, wherein the primer pair species further comprises a universal priming site.

20. The method according to claim 19, wherein the universal priming site is used for sequencing.

21. The method according to claim 1, wherein the barcode identifies the droplet.

* * * * *